United States Patent
Tuma

(10) Patent No.: US 6,610,250 B1
(45) Date of Patent: *Aug. 26, 2003

(54) APPARATUS USING HALOGENATED ORGANIC FLUIDS FOR HEAT TRANSFER IN LOW TEMPERATURE PROCESSES REQUIRING STERILIZATION AND METHODS THEREFOR

(75) Inventor: Phillip E. Tuma, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/379,165

(22) Filed: Aug. 23, 1999

(51) Int. Cl.[7] .................. A61L 2/00; F25D 17/02; F25B 29/00; B08B 9/093; C09K 3/18
(52) U.S. Cl. .................. 422/38; 422/40; 422/905; 62/114; 62/185; 62/480; 165/1; 165/5; 165/104.27; 165/104.21; 165/104.32; 252/70; 134/22.18; 134/169 R
(58) Field of Search .................. 422/38, 40, 905; 62/114, 185, 480; 165/61, 65, 104.27, 104.21, 104.32; 252/70; 134/22.18, 169 R

(56) References Cited

U.S. PATENT DOCUMENTS

| | | | |
|---|---|---|---|
| 2,500,388 A | 3/1950 | Simons | 260/614 |
| 2,519,983 A | 8/1950 | Simons | 204/62 |
| 2,594,272 A | 4/1952 | Kauck et al. | 260/333 |
| 2,616,927 A | 11/1952 | Kauck et al. | 260/563 |
| 3,250,807 A | 5/1966 | Fritz et al. | 260/535 |
| 3,250,808 A | 5/1966 | Moore, Jr. et al. | 260/535 |
| 3,274,239 A | 9/1966 | Selman | 260/514 |
| 3,656,240 A | 4/1972 | VanDijk | 34/92 |
| 3,795,986 A | 3/1974 | Sutherland et al. | 34/92 |
| 4,016,657 A | 4/1977 | Passey | 34/92 |
| 4,081,914 A | 4/1978 | Rautenbach et al. | 34/92 |
| 4,253,518 A * | 3/1981 | Minesi | |
| 4,330,033 A * | 5/1982 | Okada et al. | |
| 4,547,977 A | 10/1985 | Tenedini et al. | 34/46 |
| 4,788,339 A | 11/1988 | Moore et al. | 564/457 |
| 5,156,006 A | 10/1992 | Broderdorf et al. | 62/46.1 |
| 5,302,325 A | 4/1994 | Cheng | 261/76 |
| 5,444,102 A * | 8/1995 | Nimitz et al. | |
| 5,456,084 A | 10/1995 | Lee | 62/51.1 |
| 5,519,946 A | 5/1996 | Renzi | 34/239 |
| 5,631,306 A | 5/1997 | Dams et al. | 521/131 |
| 5,658,962 A | 8/1997 | Moore et al. | 521/114 |
| 5,701,745 A | 12/1997 | Cheng et al. | 62/51.1 |
| 5,743,023 A | 4/1998 | Fay et al. | 34/287 |
| 6,303,080 B1 * | 10/2001 | Tuma | |

FOREIGN PATENT DOCUMENTS

| | | |
|---|---|---|
| EP | 0 546 931 A1 | 6/1993 |
| EP | 0 915 311 A1 | 5/1999 |
| JP | 0092641 * | 9/1974 |
| WO | WO 96/10063 | 4/1996 |
| WO | WO 96/22356 | 7/1996 |
| WO | WO 96/36688 | 11/1996 |
| WO | WO 96/36689 | 11/1996 |
| WO | WO 97/14762 | 4/1997 |
| WO | WO 98/37163 | 8/1998 |
| WO | WO 99/14175 | 3/1999 |

OTHER PUBLICATIONS

*Encyclopedia of Chemical Technology,* Kirk–Othmer, Third Ed., vol. 10, pp. 874–881, John Wiley & Sons (1980).
*Fundamentals of Lyophilization,* Jun. 14–16, 1999 Seminar, Hull Company, A Division of S P Industries.

* cited by examiner

Primary Examiner—Robert J. Warden, Sr.
Assistant Examiner—Monzer R. Chorbaji
(74) Attorney, Agent, or Firm—Lisa M. Fagan

(57) ABSTRACT

An apparatus suitable for low temperature processing and high temperature sterilization comprising a halogenated heat-transfer fluid. The apparatus comprises an expansion device which may optionally comprise a membrane. Another embodiment of the present invention is a method therefor.

30 Claims, 8 Drawing Sheets

APPARATUS USING HALOGENATED ORGANIC FLUIDS FOR HEAT TRANSFER IN LOW TEMPERATURE PROCESSES REQUIRING STERILIZATION AND METHODS THEREFOR

FIELD OF INVENTION

This invention relates to an apparatus for low temperature processing requiring sterilization and methods therefor. More particularly, this invention relates to an apparatus (and methods therefor) using halogenated organic fluids for heat transfer in low temperature processes requiring high temperature (e.g., steam) sterilization.

BACKGROUND

Low temperature processing can generally be described as a dehydration, a chemical reaction, a biological reaction, etc. which occurs in a vessel or chamber at temperatures ranging from about −150° C. to about 0° C. The low temperature processes of particular interest in the present invention occur in a vessel or chamber which requires sterilization (or a high temperature process) at the end of the low temperature processing. Examples of such chambers include, but are not limited to, a vacuum chamber from freeze drying and a chemical or biological reactor.

Freeze drying can generally be described as a process of dehydration or of separating water from matter (e.g., biological matter or chemical matter). A product containing biological or chemical matter is frozen and then subjected to a high vacuum. The water vaporizes without melting (sublimes) leaving behind non-water components.

Generally, freeze drying requires at least four components: a vacuum chamber, a condenser, a pump, and a means for providing the heat of sublimation to the product being dried. The vacuum chamber typically contains a series of thin stainless steel shelves. Product, for example in containers, is placed upon these shelves. The condenser is used to remove the sublimed water vapor. The pump is typically a high powered vacuum pump.

A freeze drying system generally comprises other components such as a means for heat transfer. This heat transfer means may comprise a means for heating and a means for cooling. The freeze drying system typically comprises a sterilization process, especially for pharmaceutical applications.

Freeze drying systems operate over a range of temperatures, but in general the product is completely frozen prior to dehydration. The freezing point of the product may be well below the freezing point of water. For example, the freezing point of the product may be as low as about −50° C. or the operating temperature may be as low as about −50° C.

If sterilization is desired, the freeze drying system may also operate at temperatures around about 120° C. to about 130° C. (i.e., the temperature for high pressure saturated steam which is often used for sterilization).

During dehydration, a heat-transfer fluid is pumped through passages in the shelves of the vacuum chamber providing the heat of sublimation to the product being dried. Following drying, the product is removed from the container and the vacuum chamber may then be sterilized. As discussed, typically a high temperature steam (120° C. to 130° C.) is used for this sterilization process. If the heat-transfer fluid in the passages boils during this sterilization process, the system pressure may rise to a level where the shelves (which are typically thin to ensure adequate heat transfer) are damaged. Thus, selection of heat-transfer fluid is critical.

Heat-transfer fluids used in such applications typically have low viscosities at lower temperatures (i.e., −50° C. for the shelves and −80° C. for the condenser system), but are readily maintained in the liquid phase at the highest operating temperature for the system (which is typically during sterilization). Desirable heat-transfer fluids for freeze drying applications are also non-corrosive, non-toxic, and non-flammable.

Polydimethylsiloxanes (silicone oils) have a suitably wide liquid range and are often used in freeze drying. The average molecular weight of the silicone oil can be selected such that it functions well at temperatures as low as −80° C. At this temperature, the heat-transfer fluid may be pumped through passages in the shelves where the product is being dried. Such a silicone oil has a boiling point significantly above 130° C., thus the passages may be kept full of heat-transfer fluid without the danger of the heat-transfer fluid boiling and causing elevated system pressure. Silicone oils seem to be ideally suited for this type of application. However, they are flammable. There have been instances of silicone oil fires and such fires can cost millions of dollars as well as injury.

As is the case with freeze drying, during low temperature chemical or biological processes, the heat-transfer fluid preferably has good low temperature heat transfer characteristics. Typically, the heat-transfer fluid is pumped through a reactor jacket for heating, cooling, or temperature control. For ease of handling and safety, preferably this fluid is non-toxic and non-flammable. The heat-transfer fluid has similar temperature constraints (i.e., suitable at low temperature processing temperatures and at high temperature sterilization temperatures).

Halogenated organic compounds, such as perfluorocarbons (PFCs), perfluoropolyethers (PFPEs), hydrofluorocarbons (HFCs), chlorofluorocarbons (CFCs), hydrochlorofluorocarbons (HCFCs), hydrofluoroethers (HFEs), hydrohalofluoroethers (HHFEs), hydrochlorocarbons (HCCs), hydrobromocarbons (HBCs), perfluoroalkyl iodides (PFIs), perfluoroolefins (PFOs), and fluorinated compounds containing at least one aromatic moiety, or mixtures thereof are generally non-toxic and non-flammable. The lower molecular weight compounds tend to have good low temperature heat transfer properties. Additionally, halogenated organic compounds are non-corrosive and very thermally stable.

However, in conventional designs these halogenated organic compounds tend not to be viable candidates as heat-transfer fluids because either their boiling points are too low (leading to excessive system pressure at high temperatures) or their freezing points are too high (leading to freeze up or high viscosity at low temperatures). Candidates, for example, that are liquid at 130° C. or which have acceptable vapor pressures at this temperature tend to be solid or very viscous at −80° C. and thus cannot be used. Similarly, candidates, for example, that may work well at −80° C. tend to have lower boiling points which result in excessive vapor pressures that would prevent their use at 130° C. Typically, these fluids are not used in conventional designs because to maintain the fluid in a liquid state throughout the system/apparatus and throughout the operating temperature range, the system is typically pressurized above the fluid saturation pressure using a compressed gas such as air or nitrogen. This pressure compromises certain components in the apparatus unless they are built to more rigorous design codes which adds cost and may affect performance.

Thus, the need exists for an apparatus which allows volatile halogenated organic compounds having good heat transfer properties at low temperatures, non-corrosivity, non-flammability, low toxicity, etc. to be utilized in low temperature processes requiring high temperature sterilization.

SUMMARY OF THE INVENTION

The present invention provides an apparatus for low temperature processing where the chamber requires sterilization which allows a volatile halogenated organic compound to be effectively used as a heat-transfer fluid. The apparatus of the present invention allows for heat-transfer fluids to be used which have a boiling point of less than about 120° C. Thus, fluids having otherwise desirable traits can be utilized.

The present invention provides an apparatus for low temperature processing and high temperature sterilization comprising: a product; a heat-transfer fluid having a saturation temperature at a system pressure below the sterilization temperature; a chamber requiring sterilization comprising one or more passageway(s) for said heat-transfer fluid wherein said heat-transfer fluid enters and exits said passageway(s) at the lower portion of said chamber; a pump in fluid connection with said passageway(s); and an expansion device sized to accommodate the equivalent volume of heat-transfer fluid in said passageway(s) and thermal expansion of the heat-transfer fluid; wherein said expansion device is in fluid connection with said pump and said passageway(s); and wherein during the chamber sterilization a portion of the heat-transfer fluid vaporizes causing the non-vaporized portion of heat-transfer fluid to evacuate the passageway(s) in the chamber in such a way that a liquid-vapor interface forms outside of the passageway(s).

The apparatus of the present invention may further comprise an expansion device comprising a membrane to separate the heat-transfer fluid from the pressurization gas (e.g., ambient air).

Another embodiment of the present invention is an apparatus for low temperature processing and high temperature sterilization comprising: a product; a heat-transfer fluid having a saturated temperature at a system pressure below the sterilization temperature; a chamber requiring sterilization comprising one or more passageway(s) for said heat-transfer fluid; a pump in fluid connection with said passageway(s); and an expansion device sized to accommodate the equivalent volume of heat-transfer fluid in the passageway(s) and thermal expansion of the heat-transfer fluid; wherein prior to sterilization, the heat-transfer fluid is substantially evacuated from the passageway(s) by flowing into the expansion device.

Yet another embodiment of the present invention is a method of sterilizing a low temperature processing chamber comprising the steps of: (a) providing a chamber comprising one or more passageway(s); (b) providing heat-transfer fluid having a saturation temperature at a system pressure below the sterilization temperature in said passageway(s); (c) providing a means for sterilization; (d) allowing energy to flow from said means for sterilization to said heat-transfer fluid such that some of said heat-transfer fluid vaporizes; (e) after step (d), said vaporized heat-transfer fluid causing the non-vaporized heat-transfer fluid to flow to an expansion device in fluid connection with said passageways and having sufficient volume to accommodate said non-vaporized heat-transfer fluid; (f) after step (e), causing a liquid-vapor interface to form outside of said passageway(s); (g) completing the sterilization of the chamber; (h) allowing the chamber to cool; and (i) allowing the heat-transfer fluid to re-fill the passageway(s).

Another embodiment of the present invention is a method of sterilizing a low temperature processing chamber comprising the steps of: (a) providing a chamber comprising one or more passageway(s); (b) providing heat-transfer fluid having a saturation temperature at a system pressure below the sterilization temperature in said passageway(s); (c) causing said heat-transfer to leave said passageway(s) and to flow to an expansion device in fluid connection with said passageway(s) and having sufficient volume to accommodate said heat-transfer fluid from said passageway(s); (d) interrupting said fluid connection between said passageway(s) and said expansion device; (e) providing a means for sterilization; (f) sterilizing said chamber; (g) completing said sterilization; (h) allowing said chamber to cool; and (i) allowing said heat-transfer fluid to re-fill said passageway(s).

The present invention provides for either passive or actively controlled evacuation of the passageway(s). The passively-controlled system in particular may be readily retrofitted into existing systems.

Figure 1:
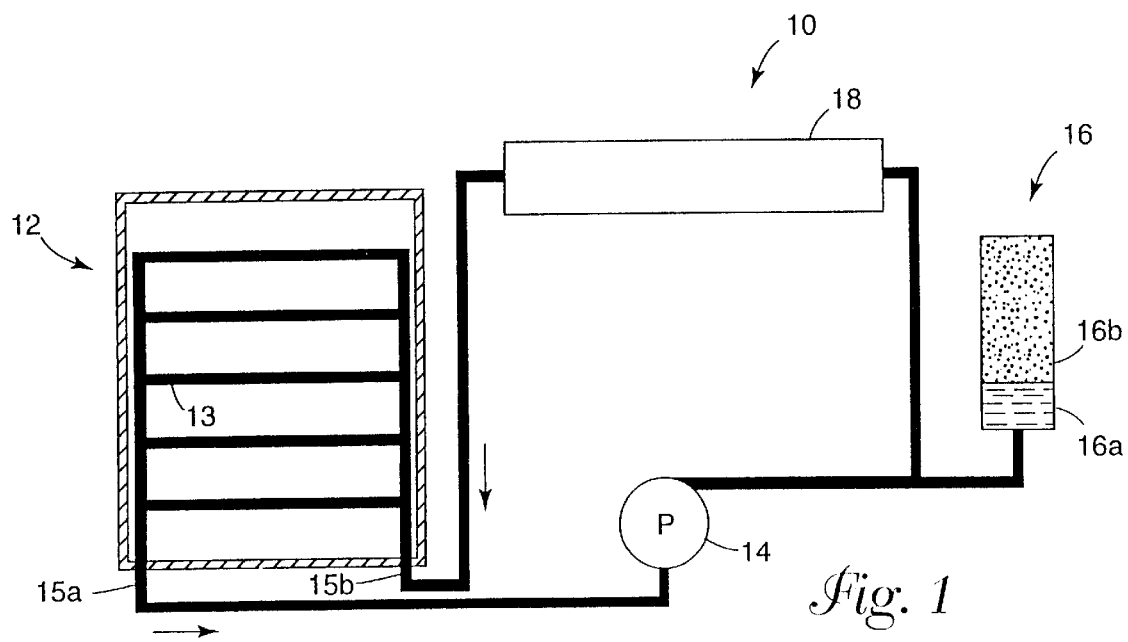
FIG. 1 is a schematic of an apparatus 10 of the present invention during low temperature operation comprising a chamber 12 having passageways 13, a thermal fluid conditioner 18, a pump 14, and an expansion device 16.

These figures are not to scale and are intended to be merely illustrative and non-limiting.

DETAILED DESCRIPTION OF ILLUSTRATIVE EMBODIMENTS

The present invention provides an apparatus for low temperature processing. The apparatus of the present invention comprises a chamber, heat-transfer system or thermal fluid conditioner, a pump, and an expansion device.

The chamber of the present invention is sterilized after completion of the low temperature processing. Sterilization is defined herein as a process for killing microorganisms which may contaminate the chamber and for removing residual biological matter from the previous cycle in a biological application.

Optionally, the apparatus may further comprise stoppering or capping systems, an automated cleaning system (e.g., multiple high pressure spray nozzles, etc.), a process control system, a series of condensers, additional pumps, etc.
Product The product of the present invention is generally a biological or a chemical material which is being processed at a low temperature, for example from about −150° C. to about 0° C. The product of the present invention is processed in a sterile environment. An example of such a material is a freeze dried pharmaceutical drug, food, biological material, parenteral (injectable) material, or delivery systems for such materials. The product may be placed directly into the chamber, or alternatively, the product may first be placed into a vial or container which is then placed in the chamber.
Heat-Transfer Fluid As discussed above, the present invention utilizes a heat-transfer fluid. The particular heat-transfer fluid will largely be chosen based on the application/system with which the apparatus will be used. The heat-transfer fluid is used to heat, cool, and/or maintain a temperature during processing. Generally, the heat-transfer fluids will be inert, non-flammable, volatile, non-aqueous, and environmentally acceptable. Additionally, the heat-transfer fluids of the present invention have good heat transfer properties at low temperatures (e.g., about −150° C. to about 0° C.). To obtain adequate heat transfer performance and manageable pumping power requirements, the viscosity of the heat-transfer fluid preferably is below about 50 cSt throughout the operating temperature range. More preferably, the viscosity is below about 30 cSt throughout this range.

The heat-transfer fluids are preferably non-flammable, which is defined herein as having a flash point of greater than about 140° F. (about 60° C.).

Preferably the apparatus is in a loop configuration to avoid heat-transfer fluid losses.

Preferably the heat-transfer fluid will be dielectric to permit the use of hermetic pumps and standard refrigerant service valves.

The heat-transfer fluids are volatile under the application conditions (i.e., during sterilization). Their boiling points will be less than about 120° C. at atmospheric pressure.

Due to flammability considerations, suitable heat-transfer fluids for use in this invention are preferably halogenated (i.e., fluorine, bromine, iodine, and/or chlorine-substituted) organic compounds. Useful halogenated organic compounds include perfluorocarbons (PFCs), perfluoropolyethers (PFPEs), hydrofluorocarbons (HFCs), hydrofluoroethers (HFEs), hydrochlorofluorocarbons (HCFCs), hydrohalofluoroethers (HHFEs), chlorofluorocarbons (CFCs), hydrochlorocarbons (HCCs), hydrobromocarbons (HBCs), perfluoroiodides (PFIs), and perfluoroolefins (PFOs), or a combination thereof. Preferably, the halogenated organic compound(s) comprise a fluorinated organic compound. Smaller amounts of flammable halogenated or flammable non-halogenated organic compounds can be incorporated in the heat-transfer fluid, provided that the resulting mixture is non-flammable.

For the present invention, CFCs are defined as compounds containing a carbon backbone substituted with carbon-bound fluorine and chlorine atoms. Until recently, liquid CFCs such as CFC-113 ($CClF_2CCl_2F$) and CFC-11 ($CCl_3F$) were considered ideal candidates for heat-transfer applications, exhibiting excellent performance, low cost, and no safety drawbacks. However, the CFCs are volatile. In addition, as of the 1987 Montreal Protocol, CFCs have been legislated out of production due to their proven degradation of the stratospheric ozone layer.

For the present invention, HCFCs are defined as compounds containing a carbon backbone substituted with carbon-bound fluorine, chlorine, and hydrogen atoms. HCFCs useful as heat transfer fluids include $CF_3CHCl_2$, $CH_3CCl_2F$, $CF_3CF_2CHCl_2$ and $CClF_2CF_2CHClF$. However, in the long term, HCFCs may also be legislated out of production due to ozone layer degradation, albeit slower than the CFCs.

For the present invention, useful PFCs include perfluorinated fluids having molecular structures which can be straight-chained, branched-chained or cyclic, or a combination thereof, such as perfluoroalkylcycloaliphatic, are fluorinated at least 95 molar percent substitution of the hydrogen atoms on the carbon chain, and are preferably free of ethylenic unsaturation. The skeletal chain of the molecular structure can contain catenary (i.e., "in-chain") oxygen, trivalent nitrogen or hexavalent sulfur heteroatoms bonded only to carbon atoms, such heteroatoms providing stable linkages between fluorocarbon groups and not interfering with the inert character of the fluid. The perfluorochemical fluid will preferably have about 5 to about 8 carbon atoms, the maximum number being dictated by the desired boiling point. Preferred PFCs typically contain about 60 to about 76 weight percent carbon-bonded fluorine. The perfluorinated fluids can be single compounds, but usually will be a mixture of such compounds. U.S. Pat. Nos. 2,500,388 (Simons); 2,519,983 (Simons); 2,594,272 (Kauck et al.); 2,616,927 (Kauck et al.); and 4,788,339 (Moore et al.), all of which are herein incorporated by reference, describe the preparation of inert perfluorinated compounds, such as perfluorinated hydrocarbons, ethers, tertiary amines and aminoethers, said preparation involving electrochemical fluorination in anhydrous HF medium. PFCs useful in this invention also include those described in *Encyclopedia of Chemical Technology*, Kirk-Othmer, Third Ed., Vol. 10, pages 874–81, John Wiley & Sons (1980).

Useful PFCs include perfluoro-4-methylmorpholine, perfluorotriethylamine, perfluoro-2-ethyltetrahydrofuran, perfluoro-2-butyltetrahydrofuran, perfluoropentane, perfluoro-2-methylpentane, perfluorohexane, perfluoro-4-isopropylmorpholine, perfluorodibutyl ether, perfluoroheptane, perfluorooctane, and mixtures thereof. Preferred inert fluorochemical liquids include perfluorohexane, perfluoro-2-butyltetrahydrofuran, perfluoroheptane, perfluorooctane, and mixtures thereof. Commercially available PFCs useful in this invention include FLUORINERT™ fluids, e.g., FC-72, FC-75, FC-77 and FC-84, described in the 1990 product bulletin #98-0211-5347-7(101.5) NPI, FLUORINERT™ fluids, (available from Minnesota Mining and Manufacturing Company, St. Paul, Minn.), and mixtures thereof.

PFPEs are polymeric compounds containing carbon, fluorine, and oxygen atoms, and are derived from the polymerization of perfluoroalkylene oxides. Useful PFPEs are described in U.S. Pat. Nos. 3,250,807 (Fritz et al.); 3,250,808 (Moore et al.); and 3,274,239 (Selman), all of which are herein incorporated by reference. Fluids derived from tetrafluoroethylene and hexafluoropropylene oxide are available as GALDEN™ HT fluids from Ausimont Corp., Thorofare, N.J.

Useful HFCs include organic compounds having a 3- to 8-carbon backbone, with a 3- to 8-carbon backbone being preferred. The carbon backbone can be straight, branched, cyclic, or mixtures of these. Useful HFCs include compounds having more than approximately 5 molar percent fluorine substitution, or less than about 95 molar percent fluorine substitution, based on the total number of hydrogen and fluorine atoms bonded to carbon, but having essentially no substitution with other atoms (e.g., chlorine) and specifically excludes PFCs, HFEs, PFOs, PFPEs, CFCs, HCFCs, and HHFEs. Useful HFCs can be selected from:

(1) compounds of Formula I:

$$C_3H_nF_{8-n}, \text{ wherein } n \leq 4 \quad (I)$$

representative compounds of Formula I include $CF_3CH_2CF_2H$, $CF_2HCF_2CH_2F$, $CH_2FCF_2CFH_2$, $CF_2HCH_2CF_2H$, $CF_2HCFHCF_2H$, $CF_3CFHCF_3$, and $CF_3CH_2CF_3$;

(2) linear or branched compounds of Formula II:

$$C_4H_nF_{10-n}, \text{ wherein } n \leq 5 \quad (II)$$

representative compounds of Formula II include $CHF_2(CF_2)_2CF_2H$, $CF_3CF_2CH_2CH_2F$, $CF_3CH_2CF_2CH_2F$, $CH_3CHFCF_2CF_3$, $CF_3CH_2CH_2CF_3$, $CH_2FCF_2CF_2CH_2F$, $CF_3CH_2CF_2CH_3$, $CHF_2CH(CF_3)CF_3$, and $CHF(CF_3)CF_2CF_3$;

(3) linear or branched compounds of Formula III:

$$C_5H_nF_{12-n}, \text{ wherein } n \leq 6 \quad (III)$$

representative compounds of Formula III include $CF_3CH_2CHFCF_2CF_3$, $CF_3CHFCH_2CF_2CF_3$, $CF_3CH_2CF_2CH_2CF_3$, $CF_3CHFCHFCF_2CF_3$, $CF_3CH_2CH_2CF_2CF_3$, $CH_3CHFCF_2CF_2CF_3$, $CF_3CF_2CF_2CH_2CH_3$, $CH_3CF_2CF_2CF_2CF_3$, $CF_3CH_2CHFCH_2CF_3$, $CH_2FCF_2CF_2CF_2CF_3$, $CHF_2CF_2CF_2CF_2CF_3$, $CH_3CF(CHFCHF_2)CF_3$, $CH_3CH(CF_2CF_3)CF_3$, $CHF_2CH(CHF_2)CF_2CF_3$, $CHF_2CF(CHF_2)CF_2CF_3$, and $CHF_2CF_2CF(CF_3)_2$;

(4) linear or branched compounds of Formula IV:

$$C_6H_nF_{14-n}, \text{ wherein } n \leq 7 \quad (IV)$$

representative compounds of Formula IV include $CHF_2(CF_2)_4CF_2H$, $(CF_3CH_2)_2CHCF_3$, $CH_3CHFCF_2CHFCHFCF_3$, $HCF_2CHFCF_2CF_2CHFCF_2H$, $H_2CFCF_2CF_2CF_2CF_2CF_2H$, $CHF_2CF_2CF_2CF_2CF_2CHF_2$, $CH_3CF(CF_2H)$ CHFCHFCF_3$, $CH_3CF(CF_3)CHFCHFCF_3$, $CH_3CF(CF_3)CF_2CF_2CF_3$, $CHF_2CF_2CH(CF_3)CF_2CF_3$, and $CHF_2CF_2CF(CF_3)CF_2CF_3$;

(5) linear or branched compounds of Formula V:

$$C_7H_nF_{16-n}, \text{ wherein } n \leq 8 \quad (V)$$

representative compounds of Formula V include $CH_3CHFCH_2CF_2CHFCF_2CF_3$, $CH_3(CF_2)_5CH_3$, $CH_3CH_2(CF_2)_4CF_3$, $CF_3CH_2CH_2(CF_2)_3$, $CH_2FCF_2CHF(CF_2)_3CF_3$, $CF_3CF_2CF_2CHFCHFCF_2CF_3$, $CF_3CF_2CF_2CHFCF_2CF_2CF_3$, $CH_3CH(CF_3)CF_2CF_2CF_2CH_3$, $CH_3CF(CF_3)CH_2CFHCF_2CF_3$, $CH_3CF(CF_2CF_3)CHFCF_2CF_3$, $CH_3CH_2CH(CF_3)CF_2CF_2CF_3$, $CHF_2CF(CF_3)(CF_2)_3CH_2F$, $CH_3CF_2CH_3$, and $CHF_2CF(CF_3)(CF_2)_3CF_3$;

(6) highly fluorinated cyclopentyl, cyclohexyl, cycloheptyl and cyclooctyl compounds, such as: $CF_3$-c-(—CF—$CF_2$—$CH_2$—$CH_2$—),

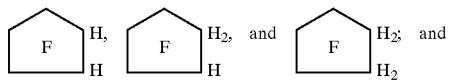

(7) linear or branched HFCs as represented below in Formula VI:

$$C_8H_nF_{18-n}, \text{ wherein } n \leq 9 \quad (VI)$$

Useful HFCs of Formula VI include $CH_3CH_2CH_2CH_2CF_2CF_2CF_2CF_3$, $CH_3(CF_2)_6CH_3$, $CHF_2CF(CF_3)(CF_2)_4CHF_2$, $CHF_2CF(CF_3)(CF_2)_4CHF_2$, $CH_3CH_2CH(CF_3)CF_2CF_2CF_2CF_3$, $CH_3CF(CF_2CF_3)CHFCF_2CF_2CF_3$, $CH_3CH_2CH_2CHFC(CF_3)_2CF_3$, $CH_3C(CF_3)_2CF_2CF_2CF_2CH_3$, $CH_3CH_2CH_2CF(CF_3)CF(CF_3)_2$ and $CH_2FCF_2CF_2CHF(CF_2)_3CF_3$.

Preferred HFCs include $CF_3CFHCFHCF_2CF_3$, $C_5F_{11}H$, $C_6F_{13}H$, $CF_3CH_2CF_2H$, $CF_3CF_2CH_2CH_2F$, $CHF_2CF_2CF_2CHF_2$, 1,2-dihydroperfluorocyclopentane and 1,1,2-trihydroperfluorocyclopentane. Useful HFCs include HFCs available under the VERTREL™, available from E. I. duPont de Nemours & Co., under the ZEORORA-H™, available from Nippon Zeon Co. Ltd., Tokyo, Japan, and under the HFC designation from AlliedSignal Chemicals, Buffalo, N.Y.

Generally the most suitable fluorinated compounds will be hydrofluoroethers, as they exhibit the best combination of good fluid heat transfer performance along with optimum safety (non-flammability and low toxicity) and environmental (non-ozone depleting and low global warming) properties. HFEs are chemical compounds containing carbon, fluorine, hydrogen, one or more ether oxygen atoms, and optionally one or more additional catenary heteroatoms within the carbon backbone, such as hexavalent sulfur or trivalent nitrogen. The HFE can be straight-chained, branched-chained, or cyclic, or a combination thereof, such as alkylcycloaliphatic. Preferably, the HFEs are free of unsaturation. These highly fluorinated ethers may be depicted by Formula VII:

$$(R_1-O)_n-R_2 \quad (VII)$$

where, in reference to Formula VII, n is a number from 1 to 3 inclusive and $R_1$ and $R_2$ are the same or are different from one another and are selected from the group consisting of alkyl, aryl, and alkylaryl groups. At least one of $R_1$ and $R_2$ contains at least one fluorine atom, and at least one of $R_1$ and $R_2$ contains at least one hydrogen atom. $R_1$ and $R_2$ may also be linear, branched, or cyclic, may contain one or more unsaturated carbon-carbon bonds, and may contain one or more catenary divalent oxygen or trivalent nitrogen atoms.

Preferred HFEs include: (1) segregated HFEs, wherein ether-bonded alkyl or alkylene, etc., segments of the HFE are either perfluorinated (e.g., perfluorocarbon) or non-fluorinated (e.g., hydrocarbon), but not partially fluorinated; and (2) non-segregated HFEs, wherein at least one of the ether-bonded segments is neither perfluorinated nor fluorine-free but is partially fluorinated (i.e., contains a mixture of fluorine and hydrogen atoms).

Segregated HFEs include HFEs which comprise at least one mono-, di-, or trialkoxy-substituted perfluoroalkane, perfluorocycloalkane, perfluorocycloalkyl-containing perfluoroalkane, or perfluorocycloalkylene-containing perfluoroalkane compound. These HFEs are described, for example, in PCT Publication No. WO 96/22356, and can be represented below in Formula VIII:

$$R_f—(O—R_h)_x \qquad \text{(VIII)}$$

wherein:

x is from 1 to about 3, and $R_f$ is a perfluorinated hydrocarbon group having a valency x, which can be straight, branched, or cyclic, etc., and preferably contains from 3 to about 7 carbon atoms, and more preferably contains from 3 to about 6 carbon atoms;

each $R_h$ is independently a linear or branched alkyl group having from 1 to about 3 carbon atoms;

wherein either or both of the groups $R_f$ and $R_h$ can optionally contain one or more catenary heteroatoms; and wherein the sum of the number of carbon atoms in the $R_f$ group and the number of carbon atoms in the $R_h$ group(s) is preferably between 4 and about 8.

Preferably, x is 1. Most preferable $R_f$ groups include $C_3F_7$-isomers, $C_4F_9$-isomers (i.e., n-, iso-, sec-, tert-), $C_5F_{11}$-isomers, $C_6F_{13}$-isomers, perfluorocyclohexyl; and most preferable $R_h$ groups include methyl, ethyl, n-propyl, and iso-propyl.

Representative compounds described by Formula VIII useful in the present invention include, but are not limited to, the following compounds:

n-$C_4F_9OCH_3$

n-$C_4F_9OC_2H_5$ n-$C_3F_7OCH_3$ $C_5F_{11}OC_2H_5$ $CF_3OC_2F_4OC_2H_5$

$(CF_3)_2CFOCH_3$ $(CF_3)_3C—OCH_3$ $(CF_3)_3C—OC_2H_5$ $(C_2F_5)_2NCF_2CF_2OCH_3$ $(CF_3)_2N(CF_2)_3OCH_3$ $(CF_3)_2N(CF_2)_2OC_2H_5$ $(C_2F_5)_2NCF_2CF_2OCH_3$

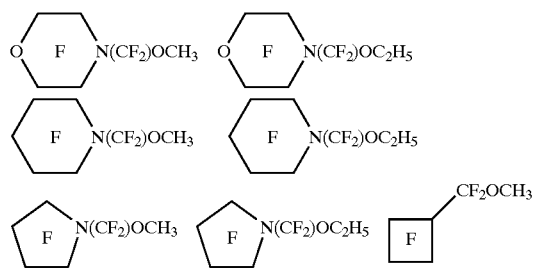

$C_2F_5CF(OCH_3)CF(CF_3)_2$ $CF_3CF(OCH_3)CF(CF_3)2$ $CF_3CF(OC_2H_5)CF(CF_3)_2$ $C_2F_5CF(OC_2H_5)CF(CF_3)_2$ $C_3F_7CF(OCH_3)CF(CF_3)_2$ wherein cyclic structures designated with an interior "F" are perfluorinated.

Particularly preferred segregated HFEs of Formula VIII include n-$C_3F_7OCH_3$, $(CF_3)_2CFOCH_3$, n-$C_4F_9OCH_3$, $(CF_3)_2CFCF_2OCH_3$, n-$C_3F_7OC_2H_5$, n-$C_4F_9OC_{2H5}$, $(CF_3)_2CFCF_2OC_2H_5$, $(CF_3)_3COCH_3$, $(CF_3)_3COC_2H_5$, $CF_3CF(OCH_3)CF(CF_3)_2$, $CF_3CF(OC_2H_5)CF(CF_3)_2$, and mixtures thereof. Segregated HFEs are available as 3M™ NOVEC™ HFE-7100 and HFE-7200 Engineered Fluids from Minnesota Mining and Manufacturing Company.

Also useful as heat transfer fluids are non-flammable azeotropes and azeotrope-like compositions which are blends of segregated HFEs with non-halogenated organic compounds. Especially useful are the azeotropes and azeotrope-like compositions consisting of blends of $C_4F_9OCH_3$, $C_4F_9OC_2H_5$ and $C_3F_7OCH_3$ with organic Such blends of $C_4F_9OCH_3$ with organic solvents are described in PCT Publication No. WO 96/36689, which is herein incorporated by reference. Useful binary $C_4F_9OCH_3$/solvent azeotropes and azeotrope-like compositions include blends of $C_4F_9OCH_3$ with the following solvents: straight chain, branched chain and cyclic alkanes having from 6 to 8 carbon atoms; cyclic and acyclic ethers having from 4 to 6 carbon atoms; acetone; chlorinated alkanes having 1, 3 or 4 carbon atoms; chlorinated alkenes having 2 carbon atoms; alcohols having from 1 to 4 carbon atoms; partially fluorinated alcohols having 2 to 3 carbon atoms; 1-bromopropane; acetonitrile; HCFC-225ca (1,1-dichloro-2,2,3,3,3-pentafluoropropane); and HCFC-225cb (1,3-dichloro-1,1,2,2,3-pertafluoropropane). Useful ternary $C_4F_9OCH_3$/solvent azeotropes and azeotrope-like compositions include blends of $C_4F_9OCH_3$ with the following solvents pairs: trans-1,2-dichloroethylene and alcohols having from 1 to 4 carbon atoms; trans-1,2-dichloroethylene and partially fluorinated alcohols having 2 to 3 carbon atoms; trans-1,2-dichloroethylene and acetonitrile; and HCFC-225 and alcohols having from 1 to 2 carbon atoms.

Such blends of $C_4F_9OC_2H_5$ with organic solvents are described in PCT Publication No. WO 96/36688, which is herein incorporated by reference. Useful binary $C_4F_9OC_2H_5$/solvent azeotropes and azeotrope-like compositions include blends of $C_4F_9OC_2H_5$ with the following solvents: straight chain, branched chain and cyclic alkanes having from 6 to 8 carbon atoms; esters having 4 carbon atoms; ketones having 4 carbon atoms; disiloxanes having 6 carbon atoms; cyclic and acyclic ethers having from 4 to 6 carbon atoms; alcohols having from 1 to 4 carbon atoms; partially fluorinated alcohols having 3 carbon atoms; chlorinated alkanes having 3 or 4 carbon atoms; chlorinated alkenes having 2 or 3 carbon atoms; 1-bromopropane; and acetonitrile.

Such blends of $C_3F_7OCH_3$ with organic solvents are described in PCT Publication No. WO 98/37163, which is herein incorporated by reference. Useful binary $C_3F_7OCH_3$/solvent azeotropes and azeotrope-like compositions include blends of $C_3F_7OCH_3$ with the following solvents: straight chain, branched chain and cyclic alkanes having from 5 to 7 carbon atoms; methyl formate; acetone; methanol; 1,1,1,3,3,3-hexafluoro-2-propanol; methylene chloride and trans-1,2-dichloroethylene. Useful ternary $C_3F_7OCH_3$/solvent azeotropes and azeotrope-like compositions include blends of $C_3F_7OCH_3$ with the following solvents pairs: trans-1,2-dichloroethylene and methanol; trans-1,2-dichloroethylene and 1,1,1,3,3,3-hexafluoro-2-propanol; methylene chloride and methanol; and methylene chloride and 1,1,1,3,3,3-hexafluoro-2-propanol.

Useful non-segregated HFEs include alpha-, beta- and omega-substituted hydrofluoroalkyl ethers such as those described in U.S. Pat. No. 5,658,962 (Moore et al.), incorporated herein by reference, which can be described by the general structure shown in Formula IX:

$$X\text{—}[R_f'\text{—}O]_yR''H \quad\quad (IX)$$

wherein:

X is either F, H, or a perfluoroalkyl group containing from 1 to 3 carbon atoms;

each $R_f'$ is independently selected from the group consisting of —$CF_2$—, —$C_2F_4$—, and —$C_3F_6$—;

R" is a divalent organic radical having from 1 to about 3 carbon atoms, and is preferably perfluorinated; and y is an integer from 1 to 7, preferably from 1 to 3; wherein when X is F, R" contains at least one F atom, and wherein the sum of the number of carbon atoms in the $R_f'$ group(s) and the number of carbon atoms in the R" group is between 4 and about 8.

Representative compounds described by Formula IX useful in the present invention include, but are not limited to, the following compounds:

$C_4F_9OC_2F_4H$ $HC_3F_6OC_3F_6H$ $HC_3F_6OCH_3$ $C_5F_{11}OC_2F_4H$ $C_6F_{13}OCF_2H$ $C_3F_7OCH_2F$ $C_3F_7O[CF(CF_3)CF_2O]_pCF(CF_3)H$, wherein $p$=0 to 1

$HCF_2OC_2F_4OCF_2H$ $HCF_2OCF_2OCF_2OCF_2H$ $HCF_2OC_2F_4OC_2F_4OCF_2H$ $HCF_2OCF_2OCF_2H$ $HCF_2OCF_2OC_2F_4OCF_2H$

Preferred non-flammable, non-segregated HFEs include $C_4F_9OC_2F_4H$, $C_6F_{13}OCF_2H$, $HC_3F_6OC_3F_6H$, $C_3F_7OCH_2F$, $HCF_2OCF_2OCF_2H$, $HCF_2OCF_2CF_2OCF_2H$, $HC_3F_6OCH_3$, $HCF_2OCF_2OC_2F_4OCF_2H$, and mixtures thereof. Non-segregated HFEs specialty liquids are available from Ausimont Corp., Milano, Italy, under the GALDEN H™.

For the present invention, HHFEs are defined as ether compounds containing fluorine, non-fluorine halogen (i.e., chlorine, bromine, and/or iodine) and hydrogen atoms. An important subclass of HHFEs is perfluoroalkylhaloethers (PFAHEs). PFAHEs are defined as ether compounds wherein on one side of the ether oxygen atom is a perfluoroalkyl group and on the other side of the ether oxygen atom is a carbon backbone substituted with carbon-bonded hydrogen atoms and halogen atoms, wherein at least one of the halogen atoms is chlorine, bromine, or iodine. Useful PFAHEs include those described by the general structure shown in Formula X:

$$R_f''\text{—}O\text{—}C_aH_bF_cX_d \quad\quad (X)$$

wherein $R_f''$ is a perfluoroalkyl group preferably having at least about 3 carbon atoms, most preferably from 3 to 6 carbon atoms, and optionally containing a catenary heteroatom such as nitrogen or oxygen; X is a halogen atom selected from the group consisting of bromine, iodine, and chlorine; "a" preferably is from about 1 to 6; "b" is at least 1; "c" can range from 0 to about 2; "d" is at least 1; and b+c+d is equal to 2a+1. Such PFAHEs are described in PCT Publication No. WO 99/14175, which is incorporated herein by reference. Useful PFAHEs include c-$C_6F_{11}$—$OCH_2Cl$, $(CF_3)_2CFOCHCl_2$, $(CF_3)_2CFOCH_2Cl$, $CF_3CF_2CF_2OCH_2Cl$, $CF_3CF_2CF_2OCHCl_2$, $(CF_3)_2 CFOCHCl_2$, $(CF_3)_2CFCF_2OCH_2Cl$, $CF_3CF_2CF_2CF_2OCHCl_2$, $CF_3CF_2CF_2CF_2OCH_2Cl$, $(CF_3)_2 CFCF_2OCHClCH_3$, $CF_3CF_2CF_2CF_2OCHClCH_3$, $(CF_3)_2 CFCF(C_2F_5)OCH_2Cl$, $(CF_3)_2CFCF_2OCH_2Br$, and $CF_3CF_2CF_2OCH_2I$.

Suitable hydrochlorocarbons and hydrobromocarbons include HCCs and HBCs such as trans-1,2-dichloroethylene, trichloroethylene, 1,1,1-trichloroethane and n-propyl bromide.

Suitable fluorinated compounds containing at least one aromatic moiety which may be useful as a co-solvent include fluorinated monoalkyl-, dialkyl- and trialkyl-substituted aromatic compounds, including toluene and xylene derivatives. Preferred among these compounds are fluoroalkyl substituted compounds, such as hexafluoroxylene, and benzotrifluoride. Such compounds are commercially available, for example, under the OXSOL™, available from Occidental Chemical Corp., Niagara Falls, N.Y.

Suitable perfluoroiodides include PFIs such as perfluoropropyl iodide ($C_3F_7I$) and perfluorobutyl iodide ($C_4F_9I$).

Perfluoroolefins (PFOs) suitable for use as heat transfer fluids are normally liquid perfluoroolefin compounds, perfluoroaromatic compounds, and perfluorocycloolefin compounds. The PFOs can contain some residual carbon-bonded hydrogen (generally less than about 0.4 mg/g and preferably less than about 0.1 mg/g, e.g., 0.01 to 0.05 mg/g) but are preferably substantially completely fluorinated. The PFOs can contain one or more catenary heteroatoms, e.g., trivalent nitrogen or divalent oxygen atoms. Representative examples of suitable blowing agent compounds include hexafluoropropene dimers, e.g., perfluoro(4-methylpent-2-ene) and perfluoro(2-methylpent-2-ene); tetrafluoroethylene oligomers, e.g., perfluoro(3-methylpent-2-ene), perfluoro(3,4-dimethylhex-3-ene), and perfluoro(1-pentene); perfluoro(2-pentene); perfluoro(1-hexene); perfluoro(2-hexene); perfluoro(3-hexene); perfluoro(1-heptene); perfluoro(2-heptene); perfluoro(3-heptene); hexafluorobenzene; octafluorotoluene; perfluorocyclopentene; isomers of $C_6F_{10}$, e.g., perfluorocyclohexene, perfluoro(1-methylcyclopentene), perfluoro(3-methylcyclopentene), and perfluoro(4-methylcyclopentene); perfluoro(1-methylcyclohexene); perfluoro(3-methylcyclohexene); perfluoro(4-methylcyclohexene); perfluoro(oxaalkenes), e.g., perfluoro(3-oxahex-1-ene), perfluoro(3-oxahept-1-ene), and perfluoro(3-oxa-4-methylpent-1-ene); perfluoro(3-ethyl-3-azapent-1-ene); and mixtures thereof. Suitable PFOs are described in U.S. Pat. No. 5,631,306, which is herein incorporated by reference.

Chamber

The chamber of the present invention is selected based on the system or application for which the apparatus of the present invention is being used. Generally, the chamber houses the product that is being processed at low temperature. The chamber of the present invention requires sterilization after the completion of the low temperature processing. The chamber may also comprise an automated cleaning system which is first used to clean the chamber prior to sterilization.

Typically, high temperature steam provides the means for sterilization. Generally, the high pressure steam with saturation temperatures ranging from about 120° C. to about 130° C. is used.

The apparatus of the present invention is particularly suitable for sterilization processes having high temperatures (e.g., those using about 120° C. to about 130° C. steam as described above).

The chamber of the present invention comprises one or more passageways. Passageways are defined herein as conduits for the heat-transfer fluid. The passageways may be within the chamber (e.g., shelves in a freeze dry vacuum chamber) or may be outside the chamber (e.g., a reactor jacket). The passageways allow the heat-transfer fluid to cool, heat, or maintain the temperature of the chamber as desired. Typically, the passageways cool down to about −150° C. to about −80° C. in the case of freeze dryers, but may reach about −150° C. for other applications such as reaction chambers.

The heat-transfer fluid preferably enters and exits the chamber passageways at the lower portion of the chamber. More preferably, the heat-transfer fluid enters and exits the chamber at the gravitational bottom of the chamber. This orientation allows substantially all of the heat-transfer fluid to leave the passageways during sterilization. This positioning allows a stable meniscus or liquid-vapor interface to form and thus flashing can be avoided.

The size, shape, and material of the chamber depend on the system or application and can be readily selected by one skilled in the art. For example, in freeze dry applications, the chamber is an insulated vacuum chamber whose walls are thick enough to withstand the pressure of the steam sterilization.

Pump

The present invention comprises a pump in fluid connection with the passageways via one or more pipes or lines. The size and type of the pump are determined by the system or application. For example, the pump may be a hermetic (e.g., canned or magnetically coupled) centrifugal pump.

Expansion Device

The expansion device is a tank or reservoir for heat-transfer fluid. The expansion device is sized to accommodate the equivalent volume of heat-transfer fluid in the passageways and the thermal expansion of the total heat-transfer fluid volume at the operating and sterilization temperatures. As discussed below, this sizing allows the system pressure to remain relatively stable during sterilization.

The expansion device is in fluid connection with the pump and the passageways. Typically the expansion device is connected to the passageways by a series of pipes or lines.

In a passively-controlled or self-regulated apparatus, the heat-transfer fluid flows into and out of the passageways. A portion of the heat-transfer fluid may flow into the expansion device when the heat-transfer fluid expands due to thermal expansion. After low temperature operation, the pump is typically shut off and the chamber is sterilized. As the temperature in the chamber rises, the temperature of the passageways rises, and thus the heat-transfer fluid temperature also rises. A portion of the heat-transfer fluid may boil and vaporize. The vapor "pushes" the liquid out of the passageways. The heat-transfer liquid is substantially displaced by the vapor in the passageways to form a liquid-vapor interface outside of the chamber (typically in a pipe or line). Typically, the heat-transfer fluid flows out of the passageways in the chamber through a pipe or line to the expansion device.

After the chamber is sterilized and cools, the heat-transfer fluid flows back into the passageways in the chamber and the cycle may be repeated without heat-transfer fluid loss.

In a passively-controlled apparatus, the system pressure remains substantially constant because of the expansion device being in fluid connection with the passageways. The system pressure can be controlled without pressurizing the system as is often necessary with conventional systems to keep the heat-transfer fluid from boiling, filling the expansion device to capacity, and causing the system pressure to rise to the point of system rupture.

Preferably, the expansion device of the present invention comprises a membrane. This membrane helps to prevent the heat-transfer fluid from leaving the apparatus or from leaking out into the air. Thus, heat-transfer fluid losses are minimized. The membrane separates the heat-transfer fluid from the gas (typically nitrogen or air) which is used to pressurize the heat-transfer fluid. The dry side of this membrane may alternatively be left open to ambient pressure and thus the system pressure will be ambient. Volatile halogenated compounds have very high gas solubilities. Without a membrane, air would likely dissolve into these halogenated organic compounds and later be evolved by the low pressure which develops at the pump inlet or during service operations. Membranes such as a bladder, diaphragm, bellows, etc. may be used.

This type of expansion tank can be readily retrofitted into existing systems without installing intricate process controls.

Alternatively, a closed expansion device may be used which optionally contains a purge valve. The purge valve allows any gas to be removed from the system and is a means for regulating system pressure.

In an actively-controlled or process-controlled apparatus, the heat-transfer fluid flows into and out of the passageways. As with the passively-controlled apparatus, a small portion of the heat-transfer fluid may flow into the expansion device during low temperature operation. After low temperature operation and prior to sterilization, the heat-transfer fluid substantially leaves the passageways. The heat-transfer fluid can be pumped out of the passageways into the expansion device or the heat-transfer fluid can be drained out of the passageways into the expansion device (depending on the physical orientation). Once the passageways are substantially evacuated, the valves between the passageways and the expansion device are shut. Then, the chamber is sterilized. Following sterilization, the valves are opened and the heat-transfer fluid re-enters the passageways. The heat-transfer fluid can be pumped into the passageways or perhaps drained into the passageways (depending on the physical orientation).

The expansion device can be a closed tank, or can have a purge valve for purging fluid and/or gas if the system pressure becomes too high.

A pressure regulator may be used in conjunction with a compressed gas source to maintain the system pressure above atmospheric pressure and/or to keep the pump from cavitating.

Thermal Fluid Conditioner

The apparatus of the present invention may further comprise a thermal fluid conditioner. The thermal fluid conditioner comprises a means for heating and/or cooling the heat-transfer fluid. The means for heating and the means for cooling can be the same unit or can be one or more separate units.

The thermal fluid conditioner may comprise a heater and a direct expansion refrigeration system or a liquid nitrogen refrigeration system. This type of system is commonly known to those skilled in the art and is to maintain the heat-transfer fluid at a prescribed temperature.

The thermal fluid conditioner is in fluid connection with the passageways.

Apparatus

The apparatus of the present invention is particularly useful for pharmaceutical freeze drying. The heat-transfer fluid is used to cool and heat the shelves in the freeze dryer (and optionally may be used to cool a condenser attached to the end of the shelves or directly attached to the vacuum chamber).

During low temperature operation or during freeze drying (FIG. 1 for example), the drying process is begun by cooling the shelves in the freeze dryer to the desired temperature using the heat-transfer fluid and the primary thermal fluid conditioning system 18 (e.g., direct expansion refrigeration cycle). The product which is placed upon the shelves 13 in vials is frozen during this process. At the same time, the condenser coil is cooled to the desired temperature to ensure an adequate potential for removing the sublimed moisture from the product.

Figure 2:
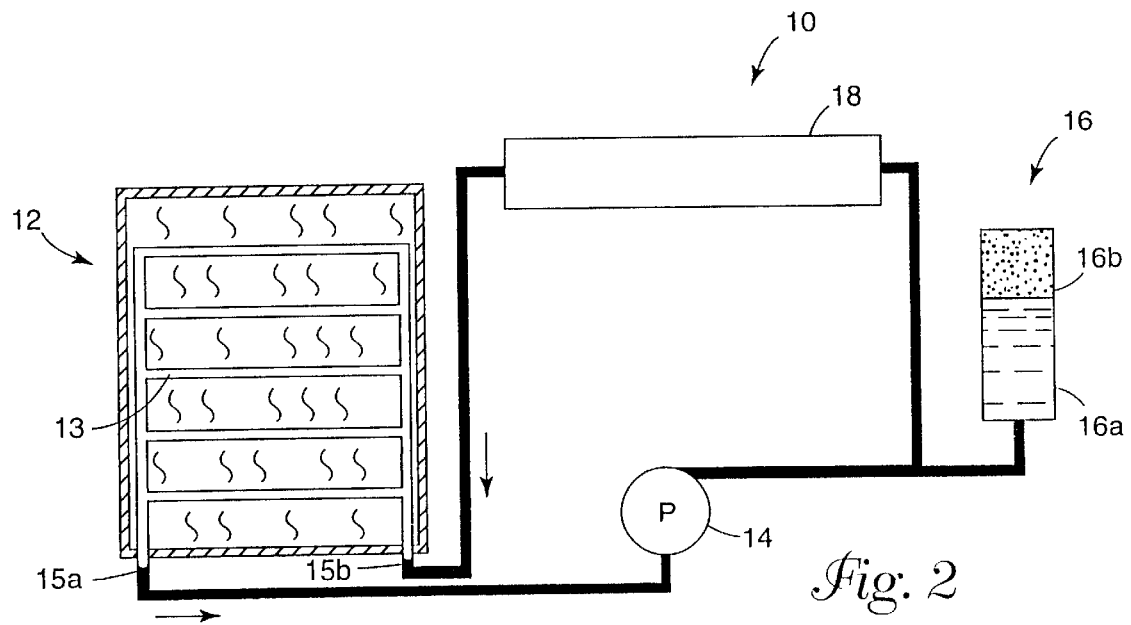
FIG. 2 is a schematic of an apparatus 10 of the present invention during sterilization comprising a chamber 12 having passageways 13, a thermal fluid conditioner 18, a pump 14, and an expansion device 16.

Vacuum is then applied to begin the drying process. During this process, the temperature of the shelves 13 is varied as desired. After drying is completed, the shelf temperature is close to room temperature, the pump 14 is turned off, the vials are stoppered, and the product is removed from the chamber 12. During low temperature operation, some heat-transfer fluid as liquid 16a and vapor 16b may be present in the expansion device 16 due to thermal expansion. The chamber 12 is now re-sealed and high pressure steam enters the freeze drying chamber (FIG. 2). When the heat-transfer fluid within the shelves reaches the saturation temperature at the system pressure, the heat-transfer fluid in the shelves begins to boil and push out the remaining liquid 15b. The displaced heat-transfer fluid from the shelves enters into the expansion device 16. The expansion device comprises liquid heat-transfer fluid 16a, and vapor heat-transfer fluid and gas (e.g., air) 16b if no membrane is used. If the membrane is utilized (between 16a and 16b), then 16a is liquid heat-transfer fluid and above the membrane is gas. This process occurs until the liquid level menisci (i.e., the liquid-vapor interface) fall below the heated chamber. As the chamber temperature increases, the heat-transfer fluid vapor remaining in the shelves superheats above the stable menisci, but preferably the system pressure does not rise more than, for example, 10 percent above its normal level (i.e., its initial pressure).

After sterilization is complete, the chamber is allowed to cool. The heat-transfer fluid vapor in the shelves will once again condense and liquid again re-fills the shelves. The cycle may then begin again.

Figure 3:
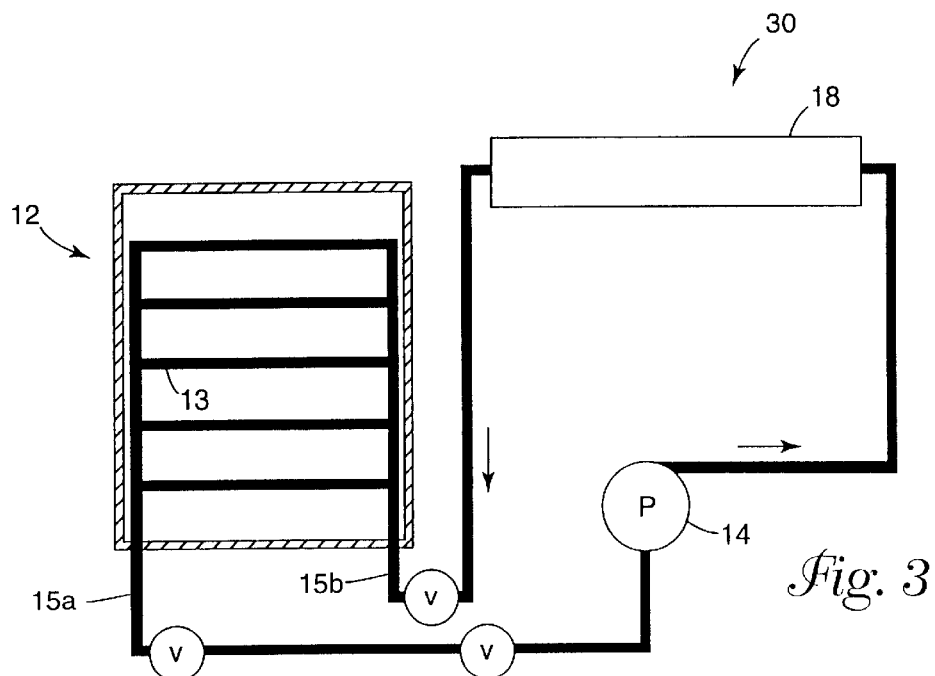
FIG. 3 is a schematic of an apparatus 30 of the present invention during low temperature operation comprising a chamber 12 having passageways 13, a thermal fluid conditioner 18, a pump 14, and an expansion device 32.
Figure 4:
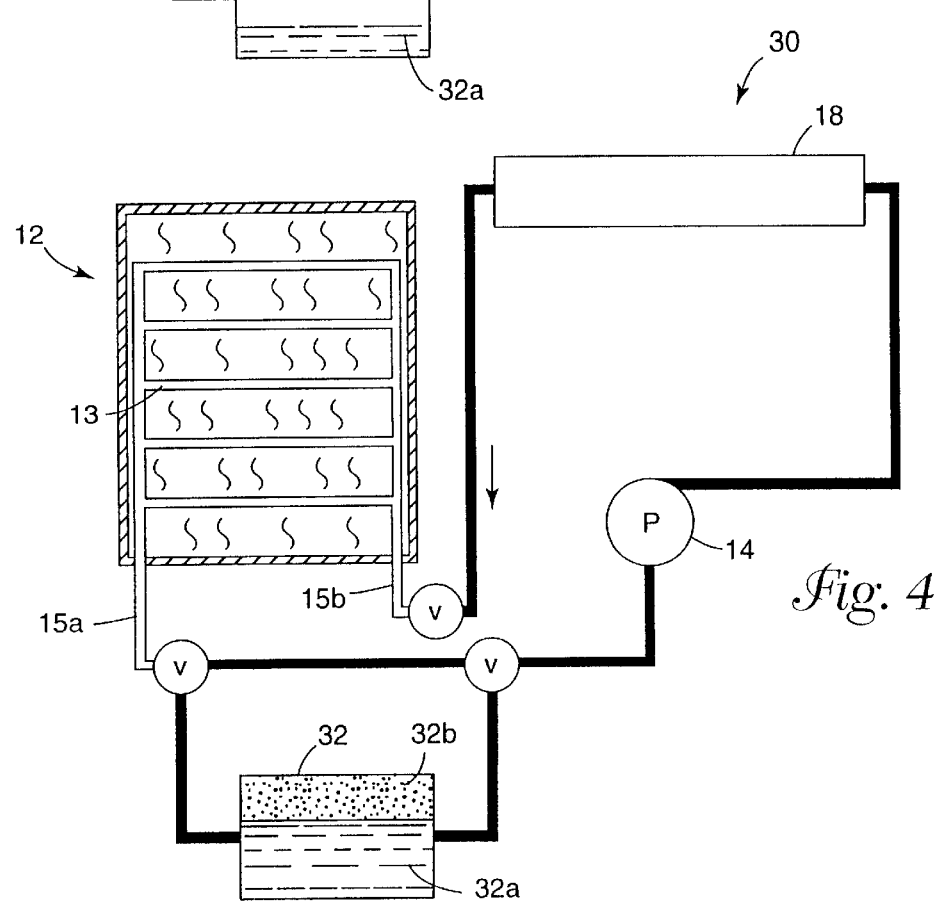
FIG. 4 is a schematic of an apparatus 30 of the present invention during sterilization comprising a chamber 12 having passageways 13, a thermal fluid conditioner 18, a pump 14, and an expansion device 32.

Another embodiment of the present invention is depicted in FIGS. 3 and 4. Here, the heat-transfer fluid exits the passageways (or shelves). Most of the heat-transfer fluid enters the expansion device 32, but some may remain in the pipes. The expansion device comprises liquid (32a) and vapor heat-transfer fluid along with gas 32b. With a membrane (between 32a and 32b), 32a is a liquid heat-transfer fluid and 32b is gas (e.g., air). Once the passageways 13 are substantially evacuated, the three key valves (the apparatus may comprise and likely will comprise additional valves) depicted in FIGS. 3 and 4 are shut. Steam them enters into the chamber. After sterilization, the key valves may then be opened and the heat-transfer fluid re-fills the passageways.

Figure 5:
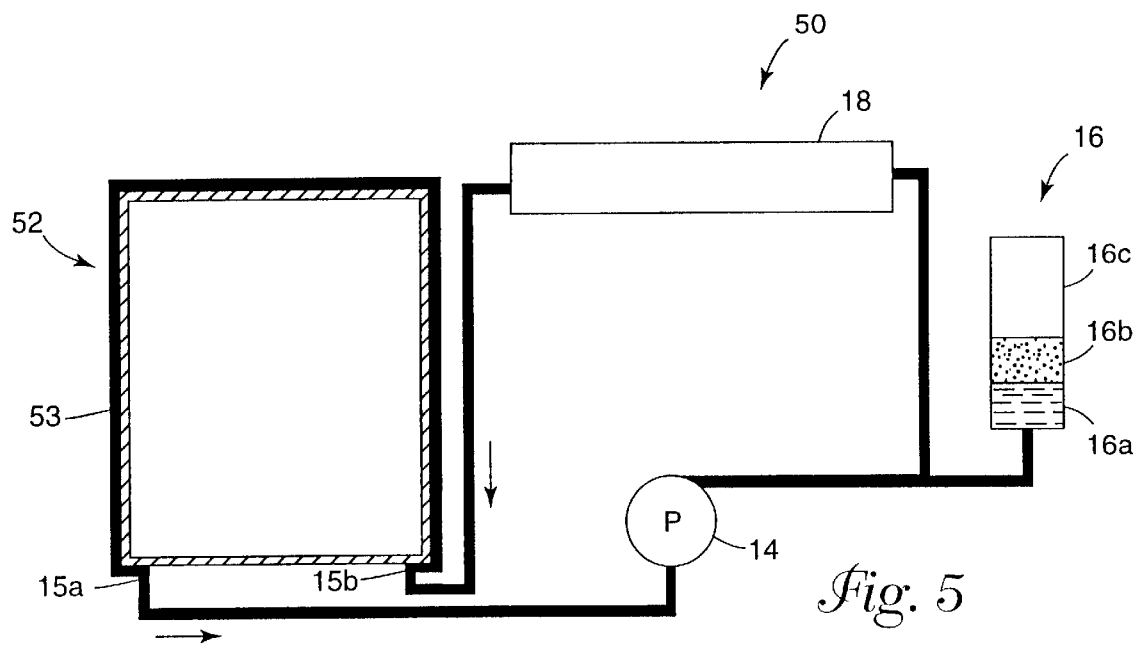
FIG. 5 is a schematic of an apparatus 50 of the present invention during low temperature operation comprising a chamber 52 having passageway 53, a thermal fluid conditioner 18, a pump 14, and an expansion device 16.
Figure 6:
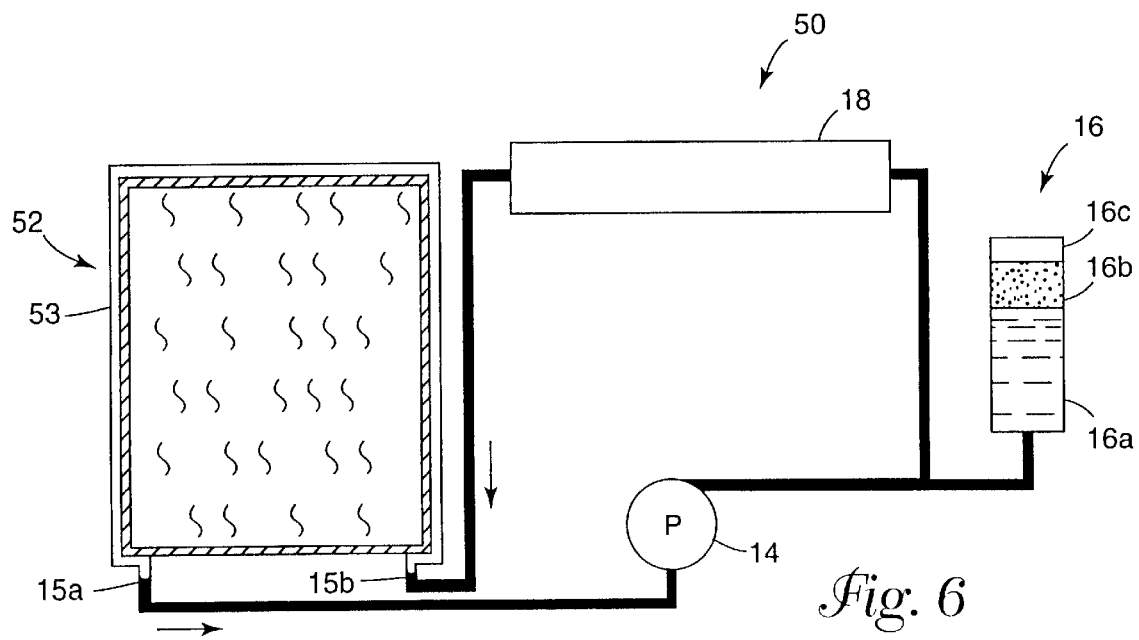
FIG. 6 is a schematic of an apparatus 50 of the present invention during sterilization comprising a chamber 52 having passageway 53, a thermal fluid conditioner 18, a pump 14, and an expansion device 16.

The apparatus of the present invention is particularly useful in low temperature reactions. This apparatus comprises a reactor vessel and a reactor jacket which comprises heat-transfer fluid. FIGS. 5 and 6 illustrate one such apparatus. During low temperature operation, the heat-transfer fluid remains in the reactor jacket 15 to perform the desired temperature-related operation. The expansion devices accommodates heat-transfer fluid 16a due to thermal expansion.

When the reaction is completed, the product is removed from the reactor chamber 52. The reactor chamber may be cleaned first and then the reactor chamber is sealed and steam enters the chamber for sterilization. As soon as the heat-transfer fluid within the reaction vessel jacket passageways reaches the saturation temperature of the heat-transfer fluid at the system pressure, the heat-transfer fluid is pushed from the passageway 53 and into the expansion device 16. The expansion device comprises liquid heat-transfer fluid 16a, and vapor heat-transfer fluid and gas 16b. If a membrane is used (between 16a and 16b), 16a is liquid heat-transfer fluid and 16b is gas. This process occurs until the liquid level menisci fall below the heated reactor chamber. As the reactor chamber temperature increases, the heat-transfer fluid vapor remaining in the passageway superheats above the stable menisci, but preferably the system pressure does not rise more than, for example, 10 percent above its normal level.

After sterilization is complete, the reactor chamber is allowed to cool. The heat-transfer fluid vapor in the passageway will once again condense and liquid again re-fills the shelves. The cycle may then begin again.

Another embodiment of the present invention comprises an expansion device and key valves (as discussed for freeze drying) used in combination with a reactor chamber.

Method

The present invention comprises a method of sterilizing a low temperature processing chamber. This method comprises the steps of: (a) providing a chamber comprising one or more passageway(s); (b) providing heat-transfer fluid having a saturation temperature at a system pressure below the sterilization temperature in said passageway(s); (c) providing a means for sterilization; (d) allowing energy to flow from said means for sterilization to said heat-transfer fluid such that some of said heat-transfer fluid vaporizes; (e) after step (d), said vaporized heat-transfer fluid causing the non-vaporized heat-transfer fluid to flow to an expansion device in fluid connection with said passageways and having sufficient volume to accommodate said non-vaporized heat-transfer fluid; (f) after step (e), causing a liquid-vapor interface to form outside of said chamber; (g) completing the sterilization of the chamber; (h) allowing the chamber to cool; and (i) allowing the heat-transfer fluid to re-fill the passageway(s).

Another embodiment of the present invention is a method of sterilizing a low temperature processing chamber comprising the steps of: (a) providing a chamber comprising one or more passageway(s); (b) providing heat-transfer fluid having a saturation temperature at a system pressure below the sterilization temperature in said passageway(s); (c) causing said heat-transfer to leave said passageway(s) and to flow to an expansion device in fluid connection with said passageway(s) and having sufficient volume to accommodate said heat-transfer fluid from said passageway(s); (d) interrupting said fluid connection between said passageway(s) and said expansion device; (e) providing a means for sterilization; (f) sterilizing said chamber; (g) completing said sterilization; (h) allowing said chamber to cool; and (i) allowing said heat-transfer fluid to re-fill said passageway(s).

EXAMPLES

The present invention will be further described with reference to the following nonlimiting examples and test methods. All parts, percentages, and ratios are by weight unless otherwise specified.

Example 1

Figure 9:
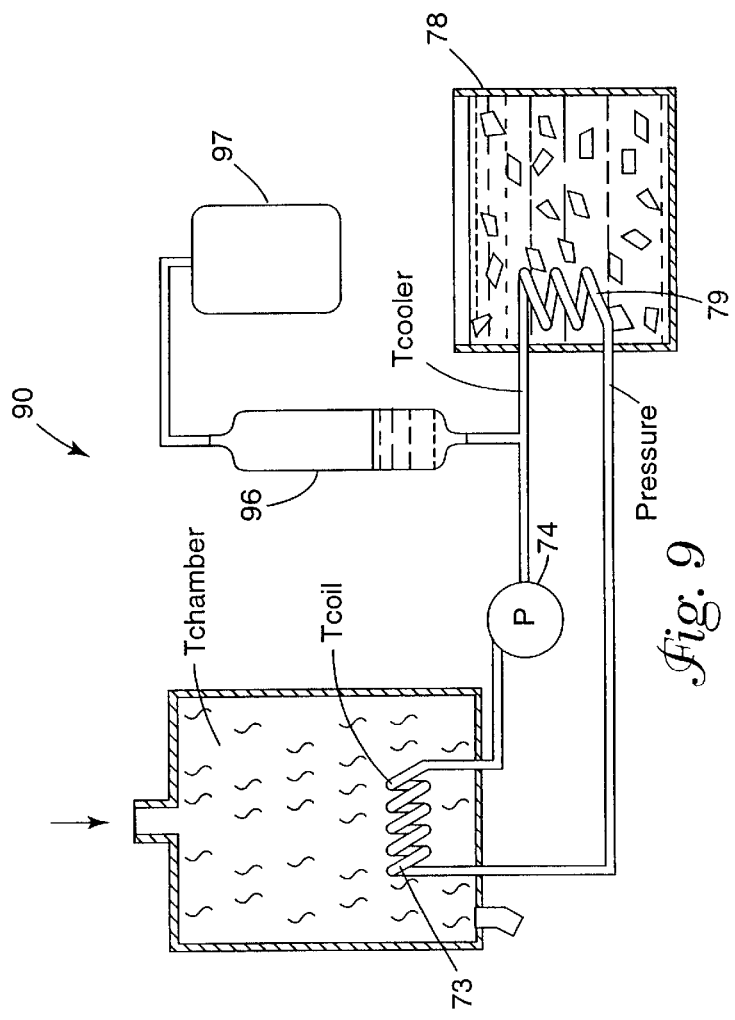
FIG. 9 is a schematic of an apparatus 90 of the present invention during sterilization comprising a chamber 72 having passageways 73, a thermal fluid conditioner 78, a pump 74, and an expansion device 96.
Figure 7:
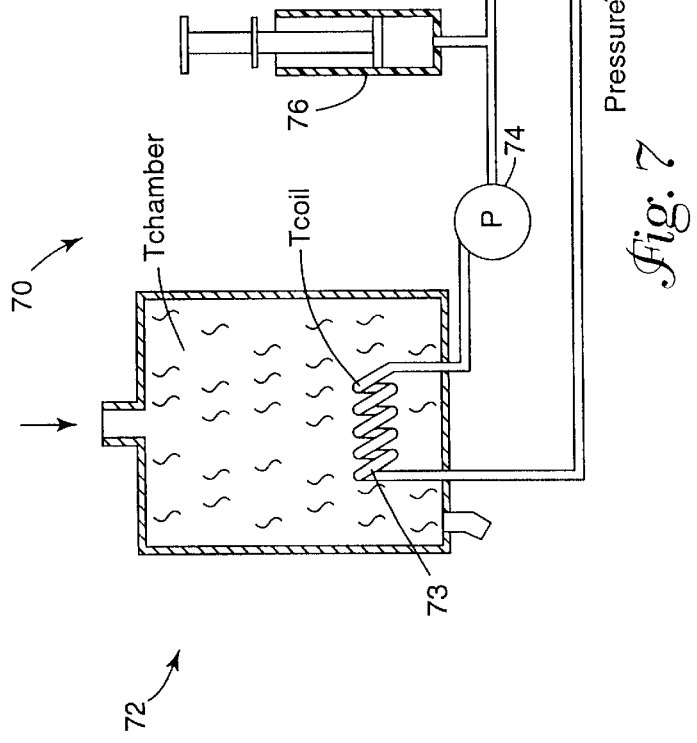
FIG. 7 is a schematic of an apparatus 70 of the present invention during sterilization comprising a chamber 72 having passageways 73, a thermal fluid conditioner 78, a pump 74, and an expansion device 76.
Figure 11:
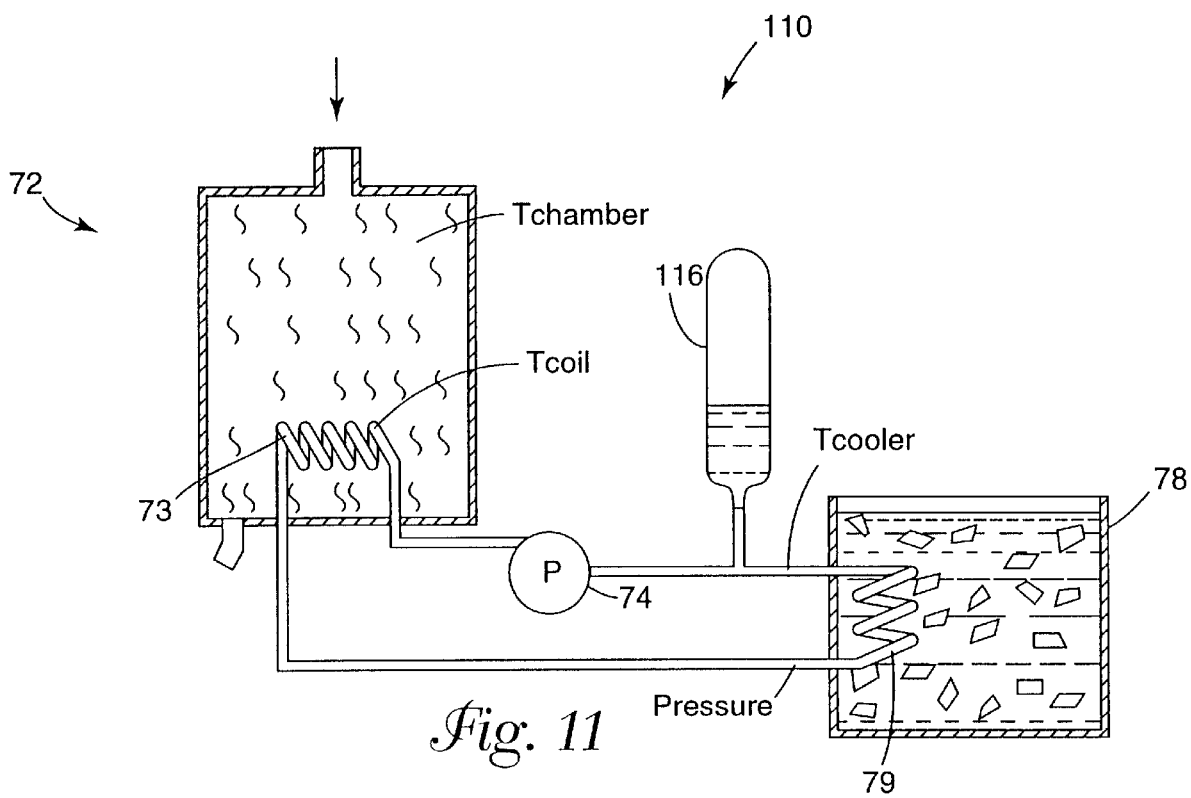
FIG. 11 is a schematic of an apparatus 110 of the present invention during sterilization comprising a chamber 72 having passageways 73, a thermal fluid conditioner 78, a pump 74, and an expansion device 116.

FIGS. 7, 9, and 11 depict apparatuses (70, 90, and 110) of the present invention as built in a laboratory. In all three, the chamber 72 is a 2 quart (1.89 liter), rectangular, polypropylene container which contains an 8 cm diameter, 5-pass coil 73 made of 0.25 inch (0.635 cm) diameter copper tubing. This coil 73 is intended to simulate the shelves of a freeze dryer or the fluid passages of a reactor vessel. Steam entered the chamber through its lid and condensate drained from the bottom of the chamber through a small hole. Saturated steam was generated in a 500 mL boiling flask with a 270 Watt heater.

The pump 74 was a Micro Pump model 81281 with a variable speed drive.

Three different expansion device configurations were used:

1. FIG. 7 depicts the first type. For operation at constant atmospheric pressure, a 75 mL Perfectum Micromate ™ ground glass syringe 76 was incorporated to simulate a bellows or bladder type expansion device which is used to maintain the apparatus at ambient or constant positive pressure.
2. FIG. 9 depicts the second type. To simulate constant pressure operation using compressed gas as a source, a 150 mL Parker E2048 316 stainless steel pressure vessel 96 was used in fluid connection with a 21.6 liter Manchester M4499 gas cylinder 97. The latter was pressurized to approximately 69 kPa gage using dry nitrogen. This combination was intended to simulate the use of a gas regulator/purge valve combination which may be used in a large industrial application to maintain positive pressure on a expansion device.
3. FIG. 11 depicts the third type. To simulate a sealed device, the 150 mL Parker E2048 316 stainless steel pressure vessel 116 was sealed after the system was filled with heat-transfer fluid.

The thermal fluid conditioner 78 was a 2 quart (1.89 liter) polypropylene container which contained an 8 cm diameter, 3-pass coil 79 made of 0.25 inch (0.635 cm) diameter copper tubing. Dry ice with a suitable heat-transfer fluid was added to this container to chill the heat-transfer fluid passing through the loop. This component was placed roughly 48 cm from the chamber as shown in FIGS. 7, 9 and 11. All fluid connections between components were made using 0.25 inch (0.635 cm) O.D. polypropylene tubing.

Temperatures were measured using 3, type-J thermocouples: Tchamber was allowed to hang freely in the chamber. Tcoil was placed in thermal contact with the top surface of the coil within the chamber. Tcooler was placed in thermal contact with the outlet line from the thermal fluid conditioner. A Paroscientific model 1001K-01 pressure transducer was installed in fluid connection with the inlet line to the thermal fluid conditioner for monitoring system pressure during sterilization.

Figure 8:
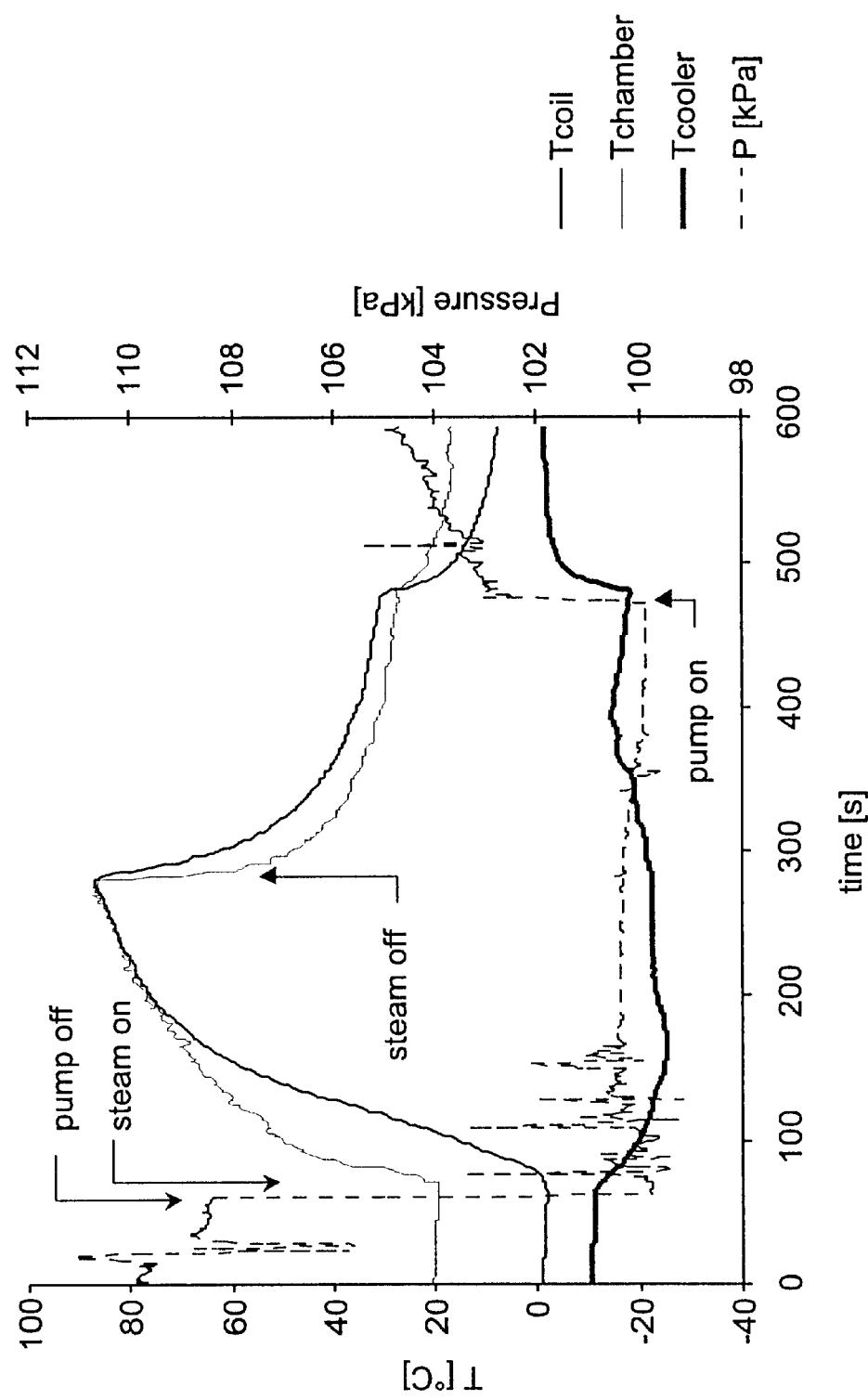
FIG. 8 is a graphical depiction of temperature and pressure values generated using the apparatus 70 depicted in FIG. 7.

FIG. 8 depicts the data trace acquired with the above apparatus operating with expansion device configuration 1 (FIG. 7) and the hydrofluoroether $C_4F_9OCH_3$ (available from Minnesota Mining and Manufacturing Company as 3M™ NOVEC™ HFE 7100) as the heat-transfer fluid. Though the system pressure dropped as expected when the pump was turned off, the admission of steam and the subsequent rise in the chamber coil temperature above the heat-transfer fluid's boiling point of 61° C. did not cause the system pressure to rise above atmospheric even though the saturation pressure of the heat-transfer fluid at 85° C. (the temperature the coil ultimately reached) is over 220 kPa. When the coil temperature reached 61° C., the plunger of the syringe was observed to displace upward by approximately 20 mL (the volume of the chamber coil). After this displacement, two menisci were visible in the inlet and outlet lines of the chamber coil just below the walls of the chamber. After the steam was turned off and the coil temperature once again fell to near 61° C., the plunger was observed to fall approximately 20 mL as the menisci rose into the chamber. Shortly after that, the pump was once again turned on.

Figure 10:
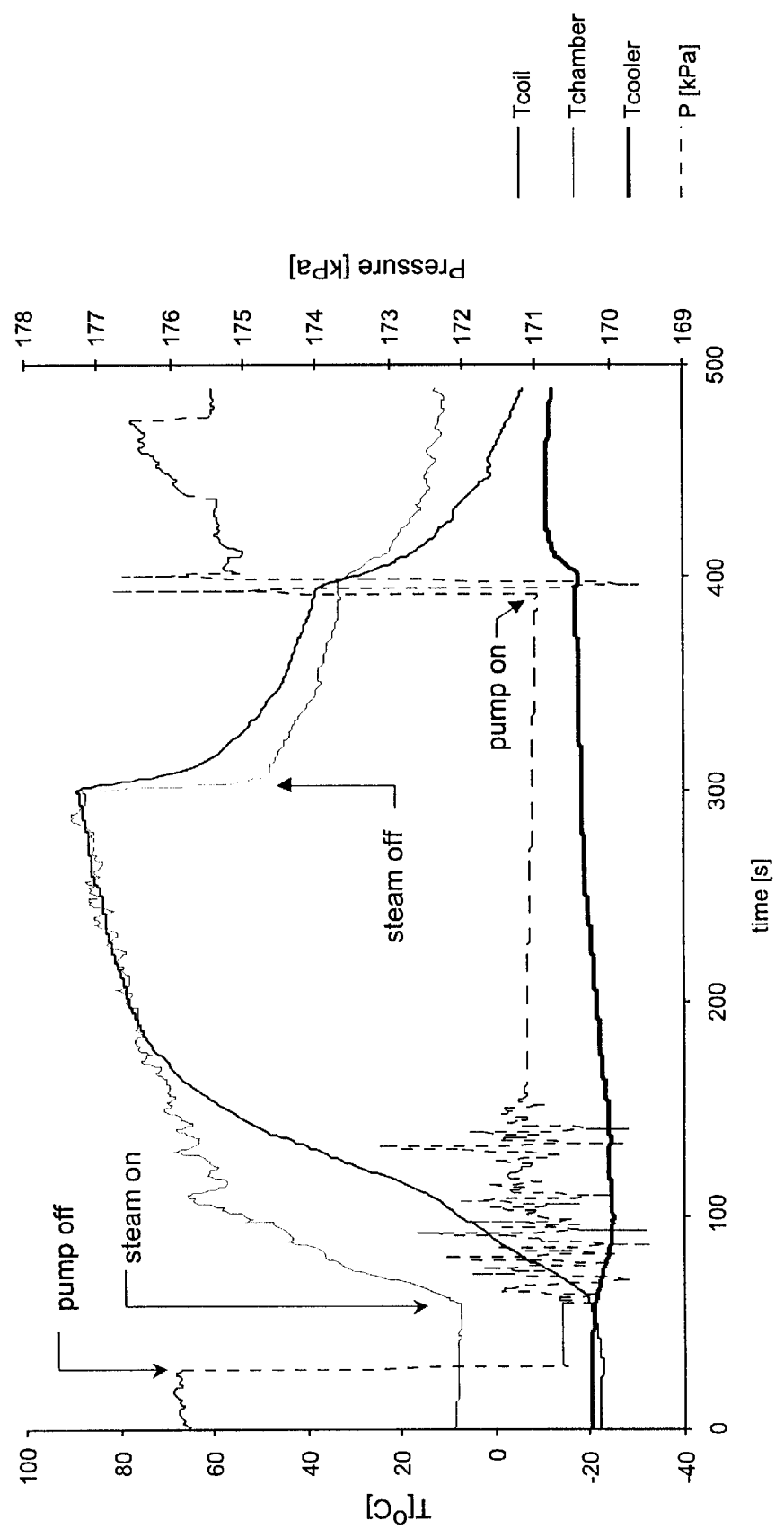
FIG. 10 is a graphical depiction of temperature and pressure values generated using the apparatus 90 depicted in FIG. 9.

FIG. 10 depicts the data trace acquired with the above apparatus operating with expansion device configuration 2 (FIG. 9) and the hydrofluorocarbon $CF_3CH_2CF_2H$ (HFC-245fa, available from AlliedSignal Chemicals, Buffalo, N.Y.) as the heat-transfer fluid. This heat-transfer fluid having a 15.3° C. boiling point is a gas at room temperature and thus the apparatus was pressurized to keep the heat-transfer fluid liquid. Once again, the system pressure did not rise above the level intentionally set with the compressed nitrogen (approximately 69 kPa gage) even though the saturation pressure of the heat-transfer fluid at 90° C. (the temperature the coil ultimately reached) is 940 kPa.

Figure 12:
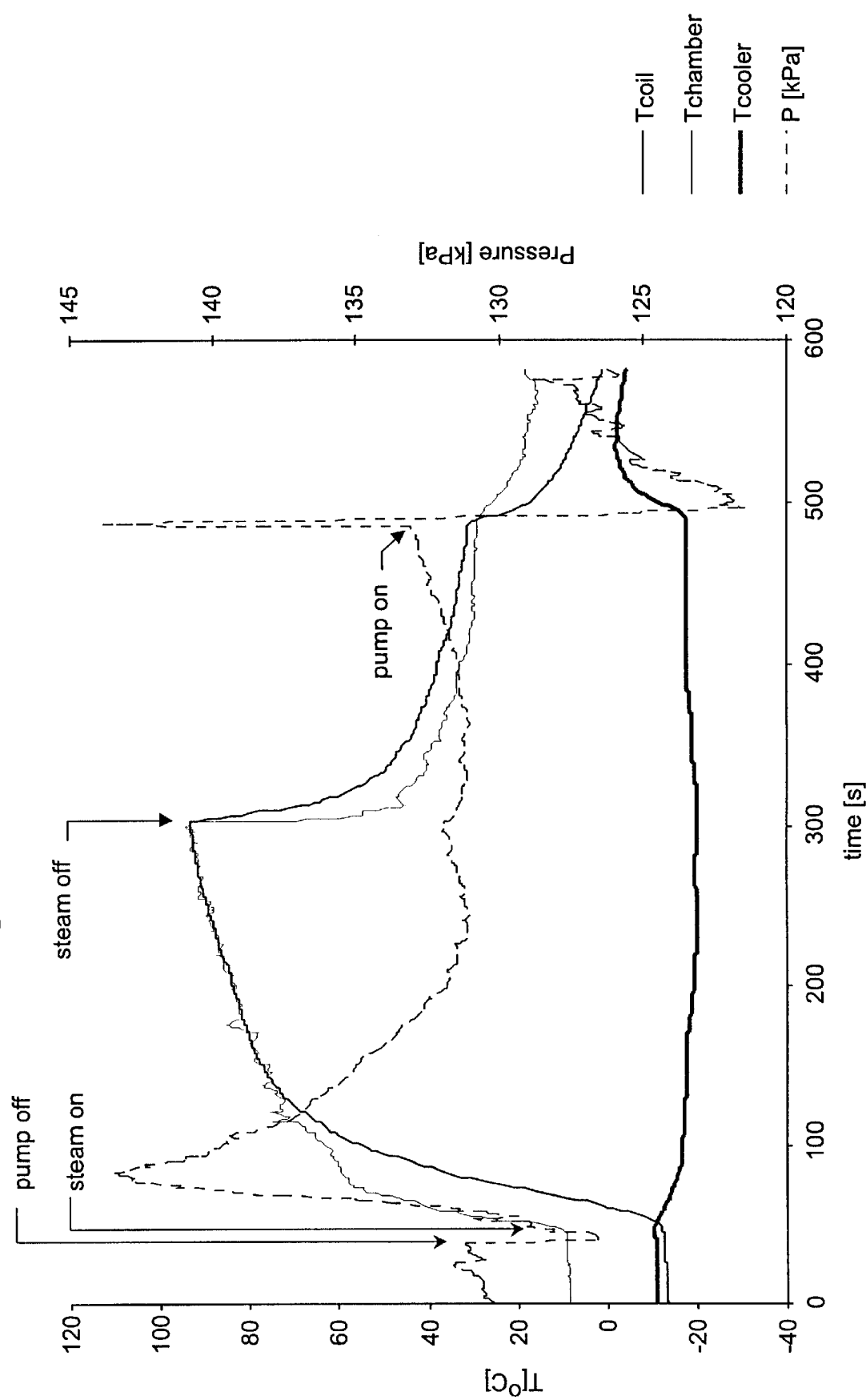
FIG. 12 is a graphical depiction of temperature and pressure values generated using the apparatus 110 depicted in FIG. 11.

FIG. 12 depicts the data trace acquired with the above apparatus operating with expansion device configuration 3 (FIG. 11) and the hydrofluorocarbon $CF_3CH_2CF_2H$ as the heat-transfer fluid. This system did not remain at constant pressure as the previous two system did. In fact, the system pressure rose initially as steam was applied to the chamber coil. Nevertheless, the system pressure did not exceed 144 kPa even though the saturation pressure of the heat-transfer fluid at 90° C. (the temperature the coil ultimately reached) is 940 kPa.

Example 2

In this Example, a freeze dryer operating with methyl-perfluorobutyl ether, a hydrofluoroether compound (available from Minnesota Mining and Manufacturing Company as 3M™ NOVEC™ HFE 7100) with an atmospheric boiling point of about 60° C. as the heat-transfer fluid is used. The heat-transfer fluid is used to cool the shelves in the freeze dryer. The total heat transfer system liquid volume is 80 gallons (303 liters) and that of the shelves within the drying chamber is 10 gallons (37.8 liters).

The expansion device is a bladder type such as those manufactured by Wellmate Division of Structural group, Chardon, Ohio. The polyurethane rubber bladder separates the heat-transfer fluid from a compressed nitrogen blanket maintained at a positive pressure of 10 psig (69 kPa gage) by a regulator and purge valve. This pressure ensures that air and moisture do not enter the system, but it is below the 15 psig limit which would mandate use of ASME-listed pressure vessels. The bladder ensures that nitrogen does not dissolve into the heat-transfer fluid. This same nitrogen (more than 40 gallons of it based on the gas solubility of the fluid) would have to be discharged from the system if maintenance required opening of the system. The expansion device is 25 gallons (94.7 liters), sufficient to accommodate thermal expansion of the entire fluid volume over the temperature range from −50° C. to 40° C. plus the volume of the shelves.

The drying process is begun by cooling the shelves in the freeze dryer to −50° C. using the heat-transfer fluid and the primary thermal fluid conditioning system which uses a direct expansion refrigeration cycle. The viscosity of the heat-transfer fluid at this temperature is 1.4 cSt, 20 percent of that of a flammable silicone oil fluid commonly used in this application. The product which is placed upon the shelves in vials is frozen during this process. At the same time, the condenser coil is cooled to −80° C. using expanded liquid nitrogen to ensure an adequate potential for removing the sublimed moisture from the product.

Vacuum is applied to begin the drying process. During this process, the temperature of the shelves is varied in accordance with a standard operating procedure. After drying is completed, the shelf temperature is close to room temperature, the pump is turned off, the vials are stoppered, and the product is removed from the chamber. The freeze drying chamber is now re-sealed and high pressure steam having a saturation temperature of 121° C. in accordance with FDA regulations is admitted to the chamber. The heat-transfer fluid within the passages of the shelves warms until it reaches 77° C., the heat-transfer fluid saturation temperature at the system pressure of 10 psig (170 kPa absolute). At this time, the heat-transfer fluid in the shelves begins to boil and push out the remaining liquid. This occurs until the liquid level menisci fall below the heated chamber and roughly 10 gallons (37.8 liters) of heat-transfer fluid has been displaced from the shelves, through the plumbing and into the expansion device. As the chamber temperature climbs still higher, the heat-transfer fluid vapor remaining in the shelves superheats above the stable menisci but the system pressure climbs no higher than 10 psig (69 kPa gage).

After sterilization is complete, the chamber is allowed to cool by radiation of heat to the surroundings. As soon as the shelf temperatures drops to 77° C., the heat-transfer fluid vapor in the shelves will once again condense allowing liquid to run in and fill the shelves. This re-filling with cool liquid aids in the shelf cooling process, reducing the waiting time required before the refrigeration system can once again be safely activated. 10 hours later, when the chamber temperature reaches 35° C., the pump and thermal conditioning systems are once again activated for the next batch of product.

In a conventional system, the expansion device would have required pressurizing to over 530 kPa (429 kPa gage) in order to maintain the heat-transfer fluid as a liquid throughout the sterilization process. This pressure would exceed the upper pressure limit required in ASME-certified pressure vessel construction and probably would have necessitated much thicker shelf walls inside the chamber, leading to poor heat transfer to and from the product vials.

Example 3

This example elucidates the concept for the same freeze dryer (Example 2) operating with HFC-245fa, $CF_3CH_2CF_2H$ a hydrofluorocarbon compound (HFC-245fa, available from AlliedSignal Chemicals) having an atmospheric boiling point of 15.3° C. The expansion device is a conventional 25-gallon (94.7 liter) sealed expansion reservoir. No attempt is made to pressurize the expansion device, but it contains a pressure relief valve to eliminate dissolved gas should such gas accumulate in the expansion device.

The apparatus is cooled as in the previous example. The viscosity of this liquid at −50° C. is 0.94 cSt, only 15 percent that of a flammable silicone oil fluid commonly used in this application. During sterilization, the system pressure is not constant. The system pressure rises quickly as the heat-transfer fluid is pushed from the shelves and vapor in the expansion device condenses. Eventually, the system pressure falls again as in the third laboratory demonstration summarized above. The pressure may, during this transient period, exceed that requiring ASME pressure vessel ratings, but it remains below the heat-transfer fluid saturation pressure at the steam sterilization temperature which is more than 700 kPa.

Example 4

This example elucidates the concept for a jacketed pharmaceutical reactor vessel operating with methyl perfluoropropyl ether, a hydrofluoroether compound having an atmospheric boiling point of 34° C. which can be prepared using the following procedure:

*Preparation of Perfluoropropyl Methyl Ether* $(C_3F_7OCH_3)$: A jacketed 1-L round bottom flask is equipped with an overhead stirrer, a solid carbon dioxide/acetone condenser and an addition funnel. The flask is charged with 85 grams (1.46 mol) of spray-dried potassium fluoride and 375 grams of anhydrous diethylene glycol and is then cooled to about −20° C. using a recirculating refrigeration system. 196 grams (1.18 mol) of $C_2F_5COF$ is added to the flask over a one hour period. The flask and its contents are warmed to about 24° C., and 184.3 grams (1.46 mol) of dimethyl sulfate is added dropwise via the addition funnel over a 45 minute period. The resulting mixture is stirred overnight at room temperature. Water (a total of 318 mL) is added dropwise to the mixture. The mixture is transferred to a 1-L round bottom flask, and the resulting ether product is azeotropically distilled. The lower product phase of the resulting distillate is separated from the upper aqueous phase, is washed once with cold water, and is subsequently distilled to give 180 grams of $C_3F_7OCH_3$ product (>99.9 percent purity by GLC). The product identity can be confirmed by GCMS and by $^1H$ and $^{19}F$ NMR.

The pharmaceutical reactor vessel contains 1000 gallons (3786 liters) of methyl perfluoropropylether and the reactor jacket holds 50 gallons (189.3 liters) of heat-transfer fluid. This apparatus is required to operate between 0 and –110° C. The two-100 gallon (378.6 liters), expansion devices are sized to accommodate thermal expansion of the heat-transfer fluid over this range plus the volume of the reactor jacket. These expansion devices are a conventional design and are vented to dry nitrogen at atmospheric pressure at the top. In the vents are placed small coils through which –80° C. expanded nitrogen passes. This minimizes the amount of heat-transfer fluid vapor which is lost as nitrogen within the expansion device is pushed out by expanding fluid.

The process begins when the first of the product reactants are added. The reactor vessel is then chilled to –110° C. using the heat-transfer fluid which has been chilled with expanded liquid nitrogen fed to the thermal fluid conditioner. The viscosity of the heat-transfer fluid at –120° C., the temperature of the cold surfaces in the thermal fluid conditioner, is only 17 cSt. When the reaction is completed, the temperature of the reacted products is increased to 5° C., at which time the product is drained from the vessel. Following a rinse with isopropyl alcohol, the reaction vessel is sealed and 121° C. steam is admitted. As soon as the heat-transfer fluid within the reaction vessel jacket passageways reaches 34° C., heat-transfer fluid is pushed from the reactor jacket. The system pressure never exceeds one atmosphere.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An apparatus for low temperature processing and high temperature sterilization comprising:
   (a) a product;
   (b) a heat-transfer fluid having a saturation temperature at a system pressure below the sterilization temperature;
   (c) a chamber requiring sterilization comprising one or more passageway(s) for said heat-transfer fluid wherein said heat-transfer fluid enters and exits said passageway(s) at the lower portion of said chamber;
   (d) a pump in fluid connection with said passageway(s); and
   (e) an expansion device sized to accommodate the equivalent volume of heat-transfer fluid in said passageway(s) and thermal expansion of the heat-transfer fluid wherein said expansion device is in fluid connection with said pump and said passageway(s);
wherein during the chamber sterilization a portion of the heat-transfer fluid vaporizes causing the non-vaporized portion of heat-transfer fluid to evacuate the passageway(s) in the chamber in such a way that a liquid-vapor interface forms outside of the passageway(s).

2. The apparatus according to claim 1, wherein said product is selected from the group consisting of a pharmaceutical drug, food, biological material, parenteral material, and a delivery system for materials.

3. The apparatus according to claim 1, wherein said low temperature processing is selected from the group consisting of freeze drying, chemical process, and biological process.

4. The apparatus according to claim 3, wherein said apparatus further comprises a thermal fluid conditioner.

5. The apparatus according to claim 4, wherein said thermal fluid conditioner comprises a means for heating said heat-transfer fluid and wherein said means is in fluid connection with said passageway(s).

6. The apparatus according to claim 4, wherein said thermal fluid conditioner comprises a means for cooling said heat-transfer fluid and wherein said means is in fluid connection with said passageway(s).

7. The apparatus according to claim 4, wherein said means of heating and means of cooling are one system.

8. The apparatus according to claim 1, wherein said low temperature processing is freeze drying and said passageway(s) are shelves contained within the chamber.

9. The apparatus according to claim 8, wherein said chamber is a vacuum chamber and said pump is a vacuum pump.

10. The apparatus according to claim 1, wherein said low temperature processing is a chemical or a biological process and wherein said passageway is a reactor jacket.

11. The apparatus according to claim 1, wherein said high temperature sterilization is high temperature steam.

12. The apparatus according to claim 1, wherein said heat-transfer fluid has an atmospheric boiling point of less than about 120° C.

13. The apparatus according to claim 1, wherein said heat-transfer fluid comprises one or more halogenated organic compound.

14. The apparatus according to claim 13, wherein said halogenated organic compound is selected form the group consisting of perfluorocarbons (PFCs), perfluoropolyethers (PFPEs), hydrofluorocarbons (HFCs), hydrofluoroethers (HFEs), hydrochlorofluorocarbons (HCFCs), hydrochlorofluoroethers (HCFEs), chlorofluorocarbons (CFCs), hydrochlorocarbons (HCCs), hydrobromocarbons (HBCs), perfluoroiodides (PFIs), perfluoroolefins (PFOs), fluorinated compounds containing at least one aromatic moiety, or a combination thereof.

15. The apparatus according to claim 14, wherein said HFEs comprise compounds of the formula

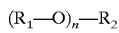

wherein:
   n is a number from 1 to 3 inclusive;
   $R_1$ and $R_2$ are the same or are different from one another and are selected from the group consisting of alkyl, aryl, and alkylaryl groups;
   at least one of $R_1$ and $R_2$ contains at least one fluorine atom;
   at least one of $R_1$ and $R_2$ contains at least one hydrogen atom; and
   $R_1$ and $R_2$ may contain one or more catenary divalent oxygen or trivalent nitrogen atoms.

16. The apparatus according to claim 14, wherein said HFEs are segregated and have the following formula:

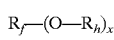

wherein:
   x is from 1 to about 3, and $R_f$ is a perfluorinated hydrocarbon group having a valency x, which can be straight, branched, or cyclic;
   each $R_h$ is independently a linear or branched alkyl group having from 1 to about 3 carbon atoms;
   wherein either or both of the groups $R_f$ and $R_h$ can optionally contain one or more catenary heteroatoms; and wherein the sum of the number of carbon atoms in the $R_f$ group and the number of carbon atoms in the $R_h$ group(s) is between 4 and about 8.

17. The apparatus according to claim 14, wherein said HFEs are non-segregated and have the following formula:

$$X-(R_f'-O)_y R''H$$

wherein:
X is either F, H, or a perfluoroalkyl group containing from 1 to 3 carbon atoms;
each $R_f'$ is independently selected from the group consisting of $-CF_2-$, $-C_2F_4-$, and $-C_3F_6-$;
R" is a divalent organic radical having from 1 to about 3 carbon atoms; and
y is an integer from 1 to 7;
wherein when X is F, R" contains at least one F atom; and wherein the sum of the number of carbon atoms in the R group(s) and the number of carbon atoms in the R" group is between 4 and about 8.

18. The apparatus according to claim 14, wherein said HFCs comprise organic compounds having a 3- to 8-carbon backbone and having about 5 to about 95 molar percent fluorine substitution based on the total number of hydrogen and fluorine atoms bonded to carbon.

19. The apparatus according to claim 14, wherein said PFCs comprise molecular structures having from about 5 to about 8 carbon atoms which can be straight-chained, branched-chained, or cyclic, or a combination thereof and which are fluorinated at least 95 molar percent substitution of the hydrogen atoms on the carbon chain.

20. The apparatus according to claim 14, wherein said halogenated organic compound is selected from the group consisting of $CF_3CH_2CF_2H$, $C_4F_9OCH_3$, $C_4F_9OC_2H_5$, $C_3F_7OCH_3$, $CF_3CHFCHFCF_2CF_3$, $HCF_2OCF_2OCF_2H$, $HCF_2OC_2F_4OCF_2H$, $HCF_2O(CF_2O)_2CF_2H$, $HCF_2OCF_2OC_2F_4OCF_2H$, $HCF_2O(C_2F_4O)_2CF_2H$,

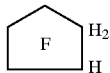

and mixtures thereof.

21. The apparatus according to claim 1, wherein said heat-transfer fluid is an binary or ternary azeotrope or azeotrope-like composition consisting of a blend of $C_4F_9OCH_3$, $C_4F_9OC_2H_5$, or $C_3F_7OCH_3$ with organic solvent(s).

22. The apparatus according to claim 1, wherein said lower portion of said chamber is the gravitational bottom of said chamber.

23. The apparatus according to claim 1, wherein said expansion device is selected from the group consisting of an open-air expansion device, a closed expansion device with a purge valve, and an expansion device comprising a membrane.

24. The apparatus according to claim 23, wherein said membrane is selected from the group consisting of polymeric bladder-type and metal bellows.

25. An apparatus for low temperature processing and high temperature sterilization comprising:
(a) a product;
(b) a heat-transfer fluid having a saturated temperature at a system pressure below the sterilization temperature;
(c) a chamber requiring sterilization comprising one or more passageway(s) for said heat-transfer fluid;
(d) a pump in fluid connection with said passageway(s); and
(e) an expansion device sized to accommodate the equivalent volume of heat-transfer fluid in the passageway(s) and thermal expansion of the heat-transfer fluid;
wherein prior to sterilization, the heat-transfer fluid is substantially evacuated from the passageway(s) by flowing into the expansion device.

26. The apparatus according to claim 25, further comprising a valve between the expansion device and the passageway(s) and wherein said valve is closed after the fluid is substantially evacuated from the passageways.

27. The apparatus according to claim 25, wherein the heat-transfer fluid is allowed to drain into the expansion device prior to sterilization.

28. The apparatus according to claim 25, wherein the heat-transfer fluid is mechanically substantially removed from the passageway(s) prior to sterilization.

29. A method of sterilizing a low temperature processing chamber comprising the steps of:
(a) providing a chamber comprising one or more passageway(s);
(b) providing heat-transfer fluid having a saturation temperature at a system pressure below the sterilization temperature in said passageway(s);
(c) providing a means for sterilization;
(d) allowing energy to flow from said means for sterilization to said heat-transfer fluid such that some of said heat-transfer fluid vaporizes;
(e) after step (d), said vaporized heat-transfer fluid causing the non-vaporized heat-transfer fluid to flow to an expansion device having sufficient volume to accommodate said non-vaporized heat-transfer fluid;
(f) after step (e), causing a liquid-vapor interface to form outside of said passageway(s);
(g) completing the sterilization of the chamber;
(h) allowing the chamber to cool; and
(i) allowing the heat-transfer fluid to re-fill the passageway(s).

30. A method of sterilizing a low temperature processing chamber comprising the steps of:
(a) providing a chamber comprising one or more passageway(s);
(b) providing heat-transfer fluid having a saturation temperature at a system pressure below the sterilization temperature in said passageway(s);
(c) causing said heat-transfer to leave said passageway(s) and to flow to an expansion device in fluid connection with said passageway(s) and having sufficient volume to accommodate said heat-transfer fluid from said passageway(s);
(d) interrupting said fluid connection between said passageway(s) and said expansion device;
(e) providing a means for sterilization;
(f) sterilizing said chamber;
(g) completing said sterilization;
(h) allowing said chamber to cool; and
(i) allowing said heat-transfer fluid to re-fill said passageway(s).

* * * * *

UNITED STATES PATENT AND TRADEMARK OFFICE
CERTIFICATE OF CORRECTION

PATENT NO.   : 6,610,250 B1
DATED        : August 26, 2003
INVENTOR(S)  : Tuma, Phillip E.

It is certified that error appears in the above-identified patent and that said Letters Patent is hereby corrected as shown below:

Column 10,
Line 35, delete "n-$C_4F_9OC_{2H5}$," and insert in place thereof -- $n$-$C_4F_9OC_2H_5$, --
Line 46, after "organic" insert -- solvents. --

Column 13,
Line 45, delete "-150ºC" and insert in place thereof -- -50ºC --

Column 16,
Line 23, delete "them" and insert in place thereof -- then --

Column 22,
Line 29, delete "form" and insert in place thereof -- from --

Column 23,
Line 17, delete "R" and insert in place thereof -- $R_f$' --

Signed and Sealed this

Thirteenth Day of April, 2004

JON W. DUDAS
*Acting Director of the United States Patent and Trademark Office*